(12) United States Patent
Lavon et al.

(10) Patent No.: US 12,349,704 B2
(45) Date of Patent: Jul. 8, 2025

(54) HIGH QUALITY CULTURED MEAT, COMPOSITIONS AND METHODS FOR PRODUCING SAME

(71) Applicant: ALEPH FARMS LTD., Rehovot (IL)

(72) Inventors: Neta Lavon, Ness Ziona (IL); Ilona Koren, Rehovot (IL)

(73) Assignee: ALEPH FARMS LTD., Rehovot (IL)

( * ) Notice: Subject to any disclaimer, the term of this patent is extended or adjusted under 35 U.S.C. 154(b) by 361 days.

(21) Appl. No.: 17/293,664

(22) PCT Filed: Nov. 14, 2019

(86) PCT No.: PCT/IL2019/051243
§ 371 (c)(1),
(2) Date: May 13, 2021

(87) PCT Pub. No.: WO2020/100143
PCT Pub. Date: May 22, 2020

(65) Prior Publication Data
US 2022/0007696 A1   Jan. 13, 2022

Related U.S. Application Data

(60) Provisional application No. 62/767,525, filed on Nov. 15, 2018.

(51) Int. Cl.
*A23L 13/40* (2023.01)
*A23J 3/22* (2006.01)

(52) U.S. Cl.
CPC .............. *A23L 13/42* (2016.08); *A23J 3/22* (2013.01); *A23L 13/45* (2016.08)

(58) Field of Classification Search
CPC .. C12N 5/0605; C12N 5/0656; C12N 5/0658; C12N 2500/38; A23J 3/22; A23L 13/40; A23L 13/42; A23L 13/45
USPC ........................................................ 426/92
See application file for complete search history.

(56) References Cited

U.S. PATENT DOCUMENTS

| | | |
|---|---|---|
| 6,406,909 B1 | 6/2002 | Shibuya |
| 2001/0043982 A1 | 11/2001 | Sakiura |
| 2004/0077086 A1 | 4/2004 | Reiter |
| 2004/0171152 A1 | 9/2004 | Price |
| 2005/0084958 A1 | 4/2005 | Vein |

(Continued)

FOREIGN PATENT DOCUMENTS

| | | |
|---|---|---|
| EP | 1180332 A1 | 2/2002 |
| EP | 2731462 B1 | 10/2015 |

(Continued)

OTHER PUBLICATIONS

Gaydhane et al., (2018) Cultured meat: state of the art and future. Biomanufacturing Reviews 3: Article No. 1.

(Continued)

*Primary Examiner* — Subbalakshmi Prakash
(74) *Attorney, Agent, or Firm* — FULLER IP LAW LLC; Rodney J. Fuller

(57) ABSTRACT

The present invention relates to the field of cultured meat, also referred to as clean meat or cell-based meat, particularly to cell cultures for producing cultured meat having sensory properties (color, taste and aroma) at least resembling whole-animal derived meat and improved nutritional value. The present invention further provides culture media for producing the cell cultures and high-quality cultured meat.

10 Claims, 4 Drawing Sheets

(56) References Cited

U.S. PATENT DOCUMENTS

| | | |
|---|---|---|
| 2005/0260748 A1 | 11/2005 | Chang |
| 2006/0286668 A1 | 12/2006 | Price |
| 2008/0064080 A1 | 3/2008 | Grillberger |
| 2011/0143432 A1 | 6/2011 | Drews |
| 2013/0029008 A1 | 1/2013 | Forgacs |
| 2014/0147555 A1 | 5/2014 | Bilet |
| 2016/0081917 A1 | 3/2016 | Ra |
| 2017/0105438 A1 | 4/2017 | Ajami |
| 2017/0121678 A1 | 5/2017 | Ruohola-Baker |
| 2017/0188612 A1 | 7/2017 | Varadan |

FOREIGN PATENT DOCUMENTS

| | | | |
|---|---|---|---|
| GB | 1380513 | A | 1/1975 |
| RU | 2506309 | C2 | 2/2014 |
| WO | 9615231 | A2 | 5/1996 |
| WO | 9815614 | A1 | 4/1998 |
| WO | 9957246 | A1 | 11/1999 |
| WO | 0003000 | A2 | 1/2000 |
| WO | 2004005493 | A1 | 1/2004 |
| WO | 2013010967 | A1 | 1/2013 |
| WO | 2015187689 | A1 | 12/2015 |
| WO | 2018189738 | A1 | 10/2018 |

OTHER PUBLICATIONS

Kadim et al., (2015) Cultured meat from muscle stem cells: A review of challenges and prospects. Journal of Integrative Agriculture 14(2): 222-233.

Prentice et al., (2013) Hydroxocobalamin association during cell culture results in pink therapeutic proteins. MAbs 5(6): 974-981.

Thomsen (2016) Proliferation and differentiation capacity of primary porcine muscle satellite cells during multiple subcultivations: A source of cells for in vitro meat production? Master Thesis, Department of Food Science—Differentiated & Biofunctional Foods, Aarhus Universitet. Retrieved from the Internet: URL: http://library.au.dk/fileadmin/www.bibliotek.au.dk/fagsider/jordbrug/Specialer/Christine_Thomsen_20092790_Master_Thesis.pdf [retrieved on Apr. 5, 2019]. 75 pages.

Ames and Elmore (1992) Aroma components of yeast extracts. Flavour and Fragrance Journal 7(2): 89-103.

Arigony et al., (2013) The influence of micronutrients in cell culture: a reflection on viability and genomic stability. Biomed Res Int 2013: 597282; 23 pages.

Bogliotti et al., (2018) Efficient derivation of stable primed pluripotent embryonic stem cells from bovine blastocysts. Proc Natl Acad Sci U S A 115(9): 2090-2095.

Bovell-Benjamin et al., (2000) Iron absorption from ferrous bisglycinate and ferric trisglycinate in whole maize is regulated by iron status. Am J Clin Nutr 71(6): 1563-1569.

Cotter et al., (2005) Bacteriocins: developing innate immunity for food. Nat Rev Microbiol 3(10): 777-788.

Daley et al., (2010) A review of fatty acid profiles and antioxidant content in grass-fed and grain-fed beef. Nutr J 9: 10; 12 pages.

Descalzo et al., (2005) Influence of pasture or grain-based diets supplemented with vitamin E on antioxidant/oxidative balance of Argentine beef. Meat Sci 70(1): 35-44.

Drackley (2004) Overview of Fat Digestion and Metabolism in Dairy Cows. University of Illinois, Urbana. 9 pages.

Esatbeyoglu and Rimbach (2017) Canthaxanthin: From molecule to function. Mol Nutr Food Res 61(6): 1600469; 17 pages.

European Food Safety Authority (EFSA) (2006) Opinion of the Scientific Panel on food additives, flavourings, processing aids and materials in contact with food (AFC) related to Ferrous bisglycinate as a source of iron for use in the manufacturing of foods ad in food supplements. EFSA Journal 4(1): 299; pp. 1-17.

Geissler and Singh (2011) Iron, meat and health. Nutrients 3(3): 283-316.

Giridhar and Parimalan (2010) A biotechnological perspective towards improvement of annatto color production for value addition—the influence of biotic elicitors. Asia-Pacific J Mol Biol Biotechnol 18: 77-79.

Haug et al., (2018) Feeding potentially health promoting nutrients to finishing bulls changes meat composition and allow for product health claims. Meat Sci 145: 461-468.

Horiguchi and Sakai (2015) Alginate Encapsulation of Pluripotent Stem Cells Using a Co-axial Nozzle. J Vis Exp (101): e52835; 7 pages.

Khoo et al., (2017) Anthocyanidins and anthocyanins: colored pigments as food, pharmaceutical ingredients, and the potential health benefits. Food Nutr Res 61(1): 1361779; 21 pages.

Krinsky and Johnson (2005) Carotenoid actions and their relation to health and disease. Mol Aspects Med 26(6): 459-516.

Layrisse et al., (2000) Iron bioavailability in humans from breakfasts enriched with iron bis-glycine chelate, phytates and polyphenols. J Nutr 130(9): 2195-2199. With erratum.

Lucarini et al., (2006) Intake of vitamin A and carotenoids from the Italian population-results of an Italian total diet study. Int J Vitam Nutr Res 76(3): 103-109.

Mehta et al., (2019) Adipogenesis from Bovine Precursors. In: Rønning S. (eds) Myogenesis. Methods in Molecular Biology, vol. 1889. Humana Press, New York, NY. pp. 111-125.

Morris et al., (1997) Short-Term Grain Feeding and its Effect on Carcass and Meat Quality. Proceedings of the New Zealand Society of Animal Production 57: 275-277.

Perez et al., (2014) Novel bacteriocins from lactic acid bacteria (LAB): various structures and applications. Microb Cell Fact 13 Suppl 1(Suppl 1): S3; 13 pages.

Rai et al., (2016) Antimicrobial peptides as natural bio-preservative to enhance the shelf-life of food. J Food Sci Technol 53(9): 3381-3394.

Rea et al., (2011) Classification of Bacteriocins from Gram-Positive Bacteria. In: Drider D., Rebuffat S. (eds) Prokaryotic Antimicrobial Peptides. Springer, New York, NY. pp. 29-53.

Savage (2012) Technology: the taste of things to come. Nature 486(7403): S18-S19.

Setser (1984) Color: reflections and transmissions12. Journal of Food Quality (6)3: 183-197.

Settanni and Corsetti (2008) Application of bacteriocins in vegetable food biopreservation. Int J Food Microbiol 121(2): 123-138.

Simonne et al., (1996) Consumer acceptability and beta-carotene content of beef as related to cattle finishing diets. J Food Sci 61(6): 1254-1257.

Strange et al., (1974) Simplified methodology for measuring meat color. Journal of Food Science 39(5): 988-992.

Szarfarc et al., (2001) Relative effectiveness of iron bis-glycinate chelate (Ferrochel) and ferrous sulfate in the control of iron deficiency in pregnant women. Arch Latinoam Nutr 51(1 Suppl 1): 42-47; 8 pages.

Trumbo (2005) Are there adverse effects of lycopene exposure? J Nutr 135(8): 2060S-2061S.

Truswell (2007) Vitamin B12. Nutrition & Dietetics vol. 64(s4): S120-S125.

Van Chuyen et al., (2012) Improvement of bixin extraction yield and extraction quality from annatto seed by modification and combination of different extraction methods. Int J Food Sci Tech 47: 1333-1338.

Vaughan et al., (2003) Functional characterization of a composite bacteriocin locus from malt isolate Lactobacillus sakei 5. Appl Environ Microbiol 69(12): 7194-7203.

Wilson and Baietto (2009) Applications and advances in electronic-nose technologies. Sensors (Basel) 9(7): 5099-5148.

Wood and Enser (1997) Factors influencing fatty acids in meat and the role of antioxidants in improving meat quality. Br J Nutr 78 Suppl 1: S49-S60.

Yang et al., (2002) Effect of vitamin E supplementation on α-tocopherol and β-carotene concentrations in tissues from pasture- and grain-fed cattle. Meat Sci 60(1): 35-40.

American Meat Science Association (AMSA). Meat Color Measurement Guidelines. Revised Dec. 2012. 136 pages.

(56) References Cited

OTHER PUBLICATIONS

3-Carotene; Handling/Processing. Technical Evaluation Report; Compiled by the Technical Services Branch for the USDA National Organic Program; Supplemented by ICF International. Apr. 20, 2012. 24 pages.

Carpenter et al., (1999) Carotenoids inhibit DNA synthesis in human aortic smooth muscle cells. FEBS Lett 447(1): 17-20.

Dennis R Conrad, Anonymous: "Vitamin B12, Cobalamin, in Cell Culture", Jul. 9, 2022 (Jul. 9, 2022), XP093155998, Retrieved from the Internet: URL:https://www.sigmaaldrich.com/DE/de/technical-documents/technical-article/cell-culture-and-cell-culture-analysis/mammalian-cell-culture/vitamin-b12. 7 pages.

HIGH QUALITY CULTURED MEAT, COMPOSITIONS AND METHODS FOR PRODUCING SAME

FIELD OF THE INVENTION

The present invention relates to the field of cultured meat, also referred to as clean meat or cell-based meat or cultivated meat, particularly to cell cultures for producing cultured meat having sensory properties (color, taste and aroma) at least resembling whole-animal derived meat, and improved nutritional value. The present invention further provides culture media for producing the cell cultures and high-quality cultured meat.

BACKGROUND OF THE INVENTION

Many expendable resources are exploited in order to sustain livestock growth, specifically cattle for meat production, including water, grain, land and energy. The world's rapidly growing population will lead to a further increase in the use of said invaluable assets. Therefore, producing meat and meat products in ways that will downsize the growth of non-human animals required to feed the entire population is highly desirable. Replacing cattle and poultry as the main meat source is also ethically beneficial since it prevents the crowded inhabitant and sometimes cruel conditions afflicted upon the cattle and poultry subjects. For these reasons, cultured meat products may also be potentially consumed by people who abstains meat for humanitarian reasons. Cultured meat is also a way to control consumed food content: nowadays, much of the farmed animals are being administered with growth hormones and antibiotics, which ends up on the consumer plates. Also, producing meat in vitro enables improving the nutritional values of the meat and making it healthier, via a control of protein content, fat amount and composition, as well as of necessary microelements and vitamins including iron, vitamin B12, and zinc. In addition, consuming meat produced under strict regulations and controlled conditions is less likely to transmit contaminations and is therefore safer for consumption. Bringing the properties of cultured cells visually, nutritionally and in flavor and aroma to at least resemble and potentially improve the properties of a meat product, while increasing the safety of the product, is a challenging task.

Supplements from the carotenoid family are known for their orange/red/brown color. Carotenoids are a family of over 600 members of naturally occurring organic pigments synthesized by plants, algae, and photosynthetic bacteria. Carotenoids can be produced from fats and other basic organic metabolic building blocks by all these organisms. Humans are not able to produce carotenoids, but they are able to accumulate carotenoids from their diet.

Carotenoids are split into two classes, xanthophylls (which contain oxygen) and carotenes (which are purely hydrocarbons, and contain no oxygen). All carotenoids are tetraterpenoids, meaning that they are produced from 8 isoprene molecules and contain 40 carbon atoms. Carotenoids that contain unsubstituted beta-ionone rings (including beta-carotene, alpha-carotene, beta-cryptoxanthin and gamma-carotene) have vitamin A activity (meaning that they can be converted to retinol).

The non-pro-vitamin-A carotenoids, including phytoene and phytofluene carotenoids from the carotene class, are the precursor carotenoids in the biosynthetic pathway of visibly colored carotenoids, for example lycopene. Carotenoids are long recognized for their health-promoting properties, typically attributed to their anti-oxidative and anti-inflammatory effects. Lycopene has been used as an antioxidant in composition for growing stem cells (for example, U.S. Patent applications Publication Nos. 20160081917 and 20050260748). It is also used as an exogenous colorant of food products.

Vitamin B12, also known as cobalamin, comprises a number of forms including cyano-, methyl-, deoxyadenosyl- and hydroxy-cobalamin. The cobalt gives this water-soluble vitamin its distinctive red color. Cobalamin is synthesized from anaerobic microorganisms, in the rumen of cattle and sheep, and humans typically consume pre-formed cobalamin from animal products, which are the main source of B12 in the diet. Cobalamin is essential for normal nervous system function, homocysteine metabolism and DNA synthesis (Truswell A S. Nutr Diet. 2007. 64(s4):S120-5125). Insufficient cobalamin can lead to morphological changes of the blood cells and the development of hematological and neurological deleterious symptoms.

Iron is one of essential micronutrients in mammal diet. It is a component of hemoglobin in erythrocytes (red blood cells), required for transporting oxygen around the body and, in the form of myoglobin, for the storage and use of oxygen in muscles (Geissler C et al.—2011. Nutrients. 3(3):283-316). The type of iron found in red meat (heme iron) is more easily absorbed and used by the body than the iron in plant foods such as nuts, seeds and leafy green vegetables (non-heme iron).

Iron supplement is a solution for low levels of iron in the body. Frequently used forms of iron in supplements include ferrous and ferric iron salts, such as ferrous sulfate, ferrous gluconate, ferric citrate, and ferric sulfate. Because of its higher solubility, ferrous iron in dietary supplements is more bioavailable than ferric iron (Murray-Kolbe L E, Beard J. in: Coates P M, Betz J M, Blackman M R, et al., eds. Encyclopedia of Dietary Supplements. 2nd ed. London and New York: Informa Healthcare; 2010:432-438).

Ferrous bisglycinate is an iron amino acid chelate. It is formed by reaction of ferrous iron with two molecules of the amino acid glycine by a covalent bound in a process called chelation. Ferrous bisglycinate is claimed to improve iron absorption, storage and increase hemoglobin level better than the conventionally used iron salts. (Bovell-Benjamin A C et al. 2000. Am. J. Clin. Nutr. 71:1563-1569; Layrisse M. et al. 2000. J. Nutr. 130(9):2195-2199 & *Erratum*, 12, 3106). Ferrous bisglycinate has been used in numerous field trials in developing countries for the iron fortification of foods providing between 2 and 23 mg/day of supplemental dietary iron without any reports of adverse effects. Additionally, dietary iron supplementation using ferrous bisglycinate, which provides approximately 15 to 120 mg iron/day, has been well tolerated by iron-deficient young children, adult males, pregnant females, and non-pregnant females with normal iron status. (The EFSA Journal (2006) 299, 1-17). Treatment with ferrous bisglycinate produced substantial improvements in the serum levels of hemoglobin and ferritin, as well as total iron binding capacity (TIBC) and iron stores in individuals who were iron deficient at the start of the fortification or supplementation trial, with no evidence of iron overloading in iron-replete individuals (Szarfarc S. C. et al. 2001. Arch. Latinoam. Nutr. 51:42-47).

Yeast extract is made up of natural components from the yeast cell: proteins, amino acids, carbohydrates, vitamins and minerals. To produce yeast extract, the contents of the yeast cell are broken down by enzymes and the cell wall is removed. Yeast extract is a food ingredient that contains many taste-providing components among them glutamate and its derivatives. It offers multiple taste-enhancement properties. Yeast extract is popular source of flavor for a range of savory food products, particularly when a meaty aroma is required (Ames J M and Elmore J S. 1992. Flavour Fragr J 7:89-103).

Rumen flora extracts are diverse group of extracts originated from defined or non-defined microorganisms constituting the flora of the bovine rumen. They are disaggregated by enzymatic reaction. In bovine the rumen is loaded by many species of bacteria that are responsible for the digestion of feed into small nutrients to be further absorbed into the cow's blood stream. The high turnover of the bacteria makes their disaggregated leftovers a part of the digested feed. Specific flora that cultures the rumen of a herd contributes to the unique taste of meat products thereof.

There is a great demand for cultured meat products that can replace meat consumption without compromising any of the beneficial properties of natural meat and provide an eating experience close to actually eating meat.

SUMMARY OF THE INVENTION

The present invention provides cultured non-human-animal derived cells, wherein the cells are enriched with exogenous supplements providing a "meat-like" color and organoleptic properties to cultured meat comprising the cells, and improving the nutritional value of the cultured meat. The present invention further provides a culture medium for producing the cultured non-human-animal derived cells, cultured meat comprising same, and products comprising the cultured meat.

The present invention is based in part on the unexpected discovery that culturing bovine-derived cells in a medium containing at least one of the exogenous supplements carotenoid (including beta ($\beta$)-carotene, lycopene, canthaxanthin) and cobalamin (vitamin B12) results in the uptake and accumulation and/or adherence of the supplement in or on the cells, thereby coloring the cells. Also, adding a specific combination of the exogenous supplements comprising at least one carotenoid and vitamin B12 to the medium of bovine-derived cells results in a cultured meat product with appearance similar to slaughtered meat. Further supplementing the medium with at least one of iron and/or a salt thereof, yeast extract and minerals (e.g. selenium and zinc and salts thereof) further provides for a meat-like flavor and aroma, and enriched nutritional values.

It is to be explicitly understood that the basal content of cultured meat comprising non-human-animal-derived cells is different from the content of meat derived from the whole animal; the teachings of the present invention provides for cultured meat having nutritional quality at least equivalent, preferably superior to that of whole-organism derived meat.

The cultured meat and products comprising same of the present invention are advantageous over currently used meat, the cultured meat comprising non-human-animal derived cells with controllable content of exogenous supplements. The products of the present invention are achieved by administering the required amount of the supplements during culturing of the cells, thereby efficiently controlling the uptake of the supplements into and/or onto the cells. Moreover, the teachings of the present invention are advantageous over previously known products mimicking meat, providing cultured meat comprising non-human-animal derived cells with the majority of the cells comprising exogenous supplements, such that the cultured meat as well as products containing same have minimal food-grade supplements added to the final cell-comprising product and may answer the "clean label" requirements.

According to one aspect, the present invention provides a non-human-animal derived cell culture comprising a plurality of non-human-animal derived cells, wherein at least 60% of the cells comprise at least one exogenous supplement selected from the group consisting of at least one natural colorant, cobalamin (vitamin B12), and a combination thereof, wherein the cell culture is characterized by a meat-like color. Each possibility represents a separate embodiment of the present invention.

It is to be explicitly understood that each of the natural colorant and vitamin B12 can contribute to the meat-like color of the cells.

According to certain exemplary embodiments, the non-human-animal derived cells comprise a combination of at least one natural colorant and Vitamin B12.

According to certain embodiments, the color of the cell culture resembles the color of myoglobin. The color of myoglobin depends on its redox status (AMSA Meat Color Measurement Guidelines, Revised December 2012).

According to certain embodiments, the color of the cell culture is brown. According to certain embodiments, the color of the cell culture is red to bright red. According to certain embodiments, the color of the cell culture is pink-purplish.

According to certain exemplary embodiments, the color of the cell culture varies in the range of brown to red. According to these embodiments, the cells of the cell culture comprise at least one compound having absorbance at a plurality of wavelengths of from about 300 nm to about 700 nm.

According to certain embodiments, the non-human-animal derived cells further comprises iron and/or a salt thereof.

According to certain embodiments, the non-human-animal derived cells further comprise at least one additional exogenous supplement selected from the group consisting of, folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention.

According to certain exemplary embodiments, the non-human-animal derived cells comprise a combination of at least one colorant, Vitamin B12 and iron and/or a salt thereof.

According to certain embodiments, the vitamin D is selected from the group consisting of vitamin D3 and vitamin D2. Each possibility represents a separate embodiment of the present invention.

According to certain embodiments, the non-human-animal derived cell culture comprise a plurality of cells providing for an amount of vitamin B12 of from about 1 mg/100 g cells to about 500 mg/100 g cells. According to some embodiments, the vitamin B12 is in amount of from 5 mg/100 g cells to about 100 mg/100 g cells.

According to certain exemplary embodiments, the fatty acid in an unsaturated fatty acid selected from the group consisting of Omega 3 [Docosahexaenoicacid (DHA), Eicosapentaenoic acid (EPA), alpha-Linolenic acid (ALA)]; Omega 6 [Linoleic acid (LA); Gamma-linolenic acid (GLA); Calendic acid; Arachidonic acid]; Omega 9 [Erucic acid/cis-13-docosenoic acid, Oleic acid, Elaidic acid] and any combination thereof. According to certain embodiments, the fatty acid is a saturated fatty acid. According to certain exemplary embodiments, the saturated fatty acid is stearic acid (18:0).

According to certain embodiments, the non-human-animal derived cells further comprise at least two, or at least three unsaturated fatty acids.

According to certain embodiments, the natural colorant is an extract obtained from at least one non-mammal organism. According to certain embodiments, the non-mammal organism is selected from the group consisting of a plant, a fungus, and an alga.

According to certain exemplary embodiments, the natural colorant is a carotenoid. According to certain embodiments, the carotenoid is selected from the group consisting of a carotene and a xanthophyll. According to additional embodiments, the natural colorant is anthocyanin.

According to some embodiment, the carotenoid is selected from the group consisting of α-carotene, β-carotene, lycopene, canthaxanthin and any combination thereof. Each possibility represents a separate embodiment of the present invention.

According to some embodiments, the non-human-animal derived cell culture comprise a plurality of cells providing for an amount of from about 0.1 mg in 100 gr cells to about 100 mg in 100 gr cells of the at least one carotenoid.

According to certain embodiments, the carotenoid is selected from the group consisting of lycopene, beta-carotene, canthaxanthin, bixin, and any combination thereof. Each possibility represents a separate embodiment of the present invention. According to certain exemplary embodiments, the carotenoid is lycopene. According to certain additional exemplary embodiments, the carotenoid is beta-carotene. According to further certain exemplary embodiments, the carotenoid is canthaxanthin. According to additional exemplary embodiments, the carotenoid is bixin. According to further exemplary embodiments, the non-human-animal derived cells comprise a combination of lycopene and canthaxanthin.

According to certain embodiments, the non-human-animal derived cells of the culture comprise a combination of at least one natural colorant and vitamin B12. According to certain exemplary embodiments, the non-human-animal derived cells of the culture comprise a combination of at least one carotenoid and vitamin B12. According to certain currently exemplary embodiments, the carotenoid is selected from the group consisting of beta-carotene, lycopene and canthaxanthin. Each possibility represents a separate embodiment of the present invention.

According to further exemplary embodiments, the non-human-animal derived cells comprise a combination of vitamin B12, canthaxanthin and lycopene.

According to certain embodiments, the non-human-animal derived cell culture comprise a plurality of cells providing for an amount of beta-carotene of from about 1 mg/100 g cells to about 100 mg/100 g cells. According to some embodiments, the beta-carotene is in amount of from 10 mg/100 g cells to about 50 mg/100 g cells.

According to certain embodiments, the non-human-animal derived cell culture comprise a plurality of cells providing for an amount of lycopene of from about 0.1 mg/100 g cells to about 50 mg/100 g cells. According to some embodiments, the lycopene is in amount of from 1 mg/100 g cells to about 20 mg/100 g cells.

According to certain embodiments, the non-human-animal derived cell culture comprise a plurality of cells providing for an amount of canthaxanthin of from about 1 mg/100 g cells to about 100 mg/100 g cells. According to some embodiments, the canthaxanthin is in amount of from 10 mg/100 g cells to about 50 mg/100 g cells.

According to certain embodiments, the non-human-animal derived cell culture comprise a plurality of cells providing for an amount of iron and/or a salt thereof of from about 0.01 mg/100 gr cells to about 50 mg/100 gr cells. According to certain embodiments, the iron is in an amount of from about 0.1 mg/100 gr cells to about 40 mg/100 gr cells. According to certain embodiments, the iron amount is from about 0.5 mg/100 gr cells to about 5 mg/100 gr cells.

According to certain embodiments, the iron is in a form selected from the group consisting of ferrous ion, ferric ion, salts thereof and heme. According to certain exemplary embodiments, the iron is in the form of ferrous bisglycinate. According to further exemplary embodiments the iron is in the form of heme.

According to certain embodiments, the non-human-animal derived cells further comprise zinc and/or a salt thereof. According to certain embodiments, the non-human animal-derived cell culture comprise a plurality of cells providing for zinc amount of from about 0.1 mg/100 gr cells to about 10 mg/100 gr cells. According to certain exemplary embodiments, the plurality of cells provides for zinc amount of from about 0.5 mg/100 g cells to about 5 mg/100 g cells.

Any method as is known in the art to measure the amount of the exogenous supplement in the non-human-animal derived cells can be used according to the teachings of the present invention. According to certain exemplary embodiments of the invention, the exogenous supplement is colored, thereby its uptake from the culture medium into and/or onto the cell and/or its amount in or on the cell can be measured by a spectrophotometer at a wavelength specific for each supplement.

It is to be explicitly understood that a cell or a plurality of cells comprising an amount of a supplement of the present invention refer to cells comprising the supplement intracellularly, within the cell membrane, adhered to the cell membrane or other cell parts and any combination thereof.

According to certain embodiments, the exogenous supplement of the present invention is a food-grade supplement. The exogenous supplement can be isolated from a natural source, or can be synthesized. According to certain currently exemplary embodiments, the exogenous supplements are food-grade suitable for human consumption.

According to certain embodiments, the non-human-animal-derived cells are pluripotent stem cells (PSCs) and/or cells differentiated therefrom.

According to further embodiments, the PSCs are induced PSCs (iPSCs) reprogrammed from somatic non-human animal cells and/or cells differentiated therefrom.

According to other embodiments, the PSCs are non-embryonic stem cells (ESCs).

According to other embodiments, the PSCs are embryonic stem cells.

According to some embodiments, the non-human-animal-derived cells are pluripotent stem cells differentiated to muscle cells. According to certain embodiments, the non-human-animal-derived cells are pluripotent stem cells differentiated to fat cells (adipocytes) and/or its progenitors. According to some embodiments, the non-human animal-derived cells are pluripotent stem cells differentiated to stromal cells (connective tissue) and/or its progenitors. According to certain embodiments, the non-human animal-derived cells are pluripotent stem cells differentiated to endothelial cells (blood vessels) and/or its progenitors.

According to some embodiments, the non-human-animal-derived cells are satellite cells differentiated to muscle cells and/or its progenitors.

According to certain embodiments, the non-human-animal derived cells are selected from the group consisting of muscle cells, fat cells, stromal cells, fibroblasts, pericytes, endothelial cells and their progenitors.

According to certain embodiments, the non-human-animal is selected from the group consisting of bovine, sheep, swine, poultry, shellfish and fish. Each possibility represents a separate embodiment of the present invention.

According to certain exemplary embodiments, the non-human-animal is a bovine. According to some exemplary embodiments, the bovine is of the species *Bos Taurus*.

According to certain embodiments, the cell culture of any one of the above-described embodiments forms cultured meat. The cultured meat may consist of the cell culture of the present invention or it may comprise additional compounds including, but not limited to a scaffold. Any edible scaffold as is known in the art for use in cultured meat can be used with the cell culture of the present invention, including edible protein scaffold, edible hydrogel scaffold, edible polysaccharide scaffold and the like. According to some embodiments, the scaffold is derived from plants, algae or microorganisms. Each possibility represents a separate embodiment of the present invention.

According to certain embodiments, the cell culture further comprises at least one additional food-grade supplement. Suitable additional supplements include, but are not limited to, saturated fatty acids, unsaturated fatty acids; lipids; flavoring agents; coloring agents; texturants; edible fibers; and the like.

According to certain exemplary embodiments, the cultured meat comprises a combination of non-human-animal-derived cells comprising muscle cells and progenitors thereof; fat cells and progenitors thereof; stromal cells and progenitors thereof; endothelial cells and progenitors thereof.

According to another aspect, the present invention provides a non-human-animal derived cell comprising at least one exogenous supplement selected from the group consisting of at least one natural colorant, cobalamin (vitamin B12) and a combination thereof, wherein the bovine-derived cell is characterized by a meat-like color.

According to further aspect, the present invention provides cultured meat comprising a plurality of non-human-animal derived cells, wherein at least 60% of the cells comprise at least one exogenous supplement selected from the group consisting of at least one natural colorant, cobalamin (vitamin B12), and a combination thereof, wherein the cultured meat is characterized by a meat-like color. According to certain exemplary embodiments, the cell culture forms cultured meat.

According to certain embodiments, the exogenous supplement is present at a site selected from the group consisting of said cell intracellular space, intramembrane space, on the cell membrane and any combination thereof.

The cell color and supplements concentrations are as described hereinabove.

According to yet another aspect, the present invention provides an enriched cell-culture liquid medium for growing non-human-animal-derived cells, the medium comprising at least one supplement selected from the group consisting of at least one natural colorant, cyanocobalamin (vitamin B12) and a combination thereof, wherein the supplement is in amount sufficient to confer meat-like color to a the non-human animal derived cells.

According to certain embodiments, the cell-culture medium comprises a combination of supplements comprising at least one colorant and vitamin B12.

According to certain embodiments, the cell-culture medium comprises a combination of supplements consisting of at least one colorant and vitamin B12.

According to certain embodiments, the enriched cell-culture liquid medium is characterized by having absorbance at a plurality of wavelengths between about 300 nm and about 700 nm.

According to yet further aspect, the present invention provides an enriched cell-culture liquid medium for growing non-human-animal derived cells, the enriched cell-culture liquid medium comprising a combination of at least one natural colorant and at least one of cobalamin (vitamin B12).

According to certain embodiments, the enriched medium of the present invention further comprises a supplement selected from the group consisting of iron and/or a salt thereof, yeast extract, bacterial extract or a combination thereof.

The at least one natural colorant is as described hereinabove.

According to some embodiments, the enriched cell-culture liquid medium further comprising at least one additional supplement selected from the group consisting of folate, zinc and/or a salt thereof, selenium and/or a salt thereof, vitamin D, vitamin E, Coenzyme Q10, at least one unsaturated fatty acid, at least one saturated fatty acid, and any combination thereof. Each possibility represents a separate embodiment of the present invention.

According to certain embodiments, the vitamin D is selected from the group consisting of vitamin D3 and vitamin D2. Each possibility represents a separate embodiment of the present invention.

According to certain exemplary embodiments, the unsaturated fatty acid is selected from the group consisting of Omega 3 fatty acids, Omega 6 fatty acids, Omega 9 fatty acids, and any combination thereof. According to certain embodiments, the enriched cell-culture liquid medium comprises at least two unsaturated fatty acids. According to certain additional or alternative embodiments, the saturated fatty acid is stearic acid.

It is to be explicitly understood that the supplements of the medium as described hereinabove are in addition to supplements present in the yeast or bacterial extract.

According to some embodiments, the enriched medium comprises the at least one carotenoid at a concentration of from about 0.1 µg/ml to about 50 mg/ml.

According to certain embodiments, the carotenoid concentration in the medium is from about 1 µg/ml to about 10 mg/ml. According to certain exemplary embodiments, the enriched medium comprises the at least one carotenoid at a concentration of from about 1 µg/ml to about 5 mg/ml. According to certain further exemplary embodiments, the enriched medium comprises the at least one carotenoid at a concentration of from about 1 µg/ml to about 1.5 mg/ml.

According to some embodiments, the enriched medium comprises the vitamin B12 at a concentration of from about 0.5 mg/ml to 100 mg/ml. According to certain exemplary embodiments, the enriched medium comprises the vitamin B12 at a concentration of from about 1 mg/ml to about 50 mg/ml. According to other exemplary embodiments, the enriched medium comprises the vitamin B12 at a concentration of from about 1 mg/ml to about 15 mg/ml.

According to some embodiments, the enriched medium comprises the yeast extract at a concentration of from about 10 µg/ml to about 5 g/ml. According to certain exemplary embodiments, the enriched medium comprises yeast extract at a concentration of from about 50 µg/ml to about 1 g/ml. According to certain exemplary embodiments, the enriched medium comprises yeast extract at a concentration of from about 500 µg/ml to about 50 mg/ml.

According to some embodiments, the enriched medium comprises the iron and/or a salt thereof at a concentration of from about 100 µg/ml to about 1,250 µg/ml. According to certain exemplary embodiments, the enriched medium comprises the iron salt at a concentration of from about 100 µg/ml to about 1000 µg/ml.

According to some embodiments, the enriched medium comprises the zinc or the salt thereof at a concentration of from about 0.1 µg/ml to about 50 µg/ml. According to some embodiments, the enriched medium comprises the zinc or the salt thereof at a concentration of from about 0.1 µg/ml to about 15 µg/ml.

According to yet additional aspect, the present invention provides a method for producing cultured meat characterized by meat-like color, the method comprising culturing non-human-animal derived cells in the enriched medium of the present invention.

According to certain embodiments, the enriched medium comprises at least one natural colorant, Vitamin B12, iron and/or a salt thereof, yeast extract, bacterial extract or a combination thereof. According to these embodiments, the cultured meat is further characterized by sensory properties similar to non-human-animal derived meat.

It is to be understood that any combination of each of the aspects and the embodiments disclosed herein is explicitly encompassed within the disclosure of the present invention.

Other objects, features and advantages of the present invention will become clear from the following description and drawings.

BRIEF DESCRIPTION OF THE FIGURES

FIG. 1 demonstrates beta-carotene uptake from the medium into bovine cells.

DETAILED DESCRIPTION OF THE INVENTION

Figure 1A:
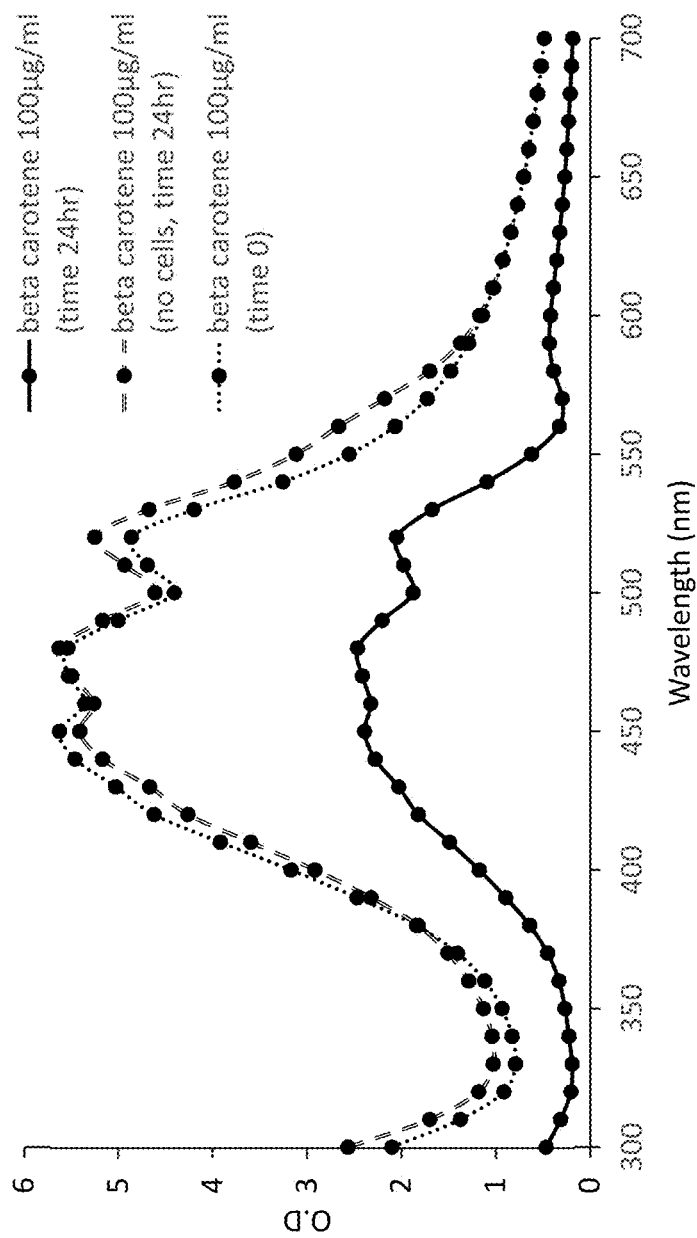
FIG. 1A: initial concentration of 100 µg beta-carotene per ml growth medium.

In the recent decade, the need for cultured meat and products thereof has been acknowledged, yet high quality, affordable products are not available. The present invention provides compositions and methods taking the efforts to obtain such product a step ahead, improving the growth rate, taste, aroma, color and nutritional value of non-human-animal derived cell cultures forming cultured meat.

For convenience and clarity certain terms employed in the specification, examples, and claims are described herein.

Definitions

The terms "clean meat" or "cultured meat" or "in-vitro meat" are interchangeably used herein to describe meat grown from in vitro non-human, animal cell culture, instead of from slaughtered animals. Additional terms that may be used in the art to describe meat grown from in vitro animal cell culture include lab-grown meat, test tube meat, tube steak, synthetic meat, cell-cultured meat, tissue engineered meat, engineered meat, artificial meat, meat analog and manmade meat.

As used herein the term "exogenous" with regard to a supplement refers to a substance/compound which is taken up by a cell from a culture medium. The exogenous supplement can be a compound naturally present within the cell (endogenous compound) or a compound not naturally found in a non-human-animal-derived cell (heterologous compound).

As used herein, the term "natural colorant" refers to a pigment that can be found in natural sources, including plants, algae, fungi and the like. It is to be explicitly understood that the natural colorant of the present invention can be derived from the natural source or can be synthesized chemically.

The terms "meat" when used alone; "meat-like"; and "non-human-animal derived meat" are used herein interchangeably and refer to meat derived from a non-human-animal, including bovine, sheep, swine, poultry, shellfish and fish.

As used herein, the term "sensory properties" with regard to meat and/or cultured meat refers to the appearance, taste, aroma and texture of the neat/cultured meat.

As used herein the term "pluripotent stem cells (PSCs)" refers to cells that can propagate indefinitely, as well as give rise to every other cell type in the body.

As used herein the term "induced pluripotent stem cells (iPSCs)" refers to a type of pluripotent stem cell that can be generated directly from differentiated cells by reprogramming process.

As used herein the term "embryonic stem cells (ESC)" refers to a type of pluripotent stem cell derived from blastocyst.

The term "reprogramming" refers to conversion of one specific cell type to another. According to certain embodiments of the present invention, reprogramming is the conversion of a somatic cell type, to a pluripotent stem cell type known as an induced pluripotent stem cell, or iPSC.

According to one aspect, the present invention provides a cell culture comprising a plurality of non-human-animal-derived cells, wherein at least 60% of the cells comprise at least one exogenous supplement selected from the group consisting of at least one natural colorant, cobalamin (vitamin B12), and a combination thereof, wherein the cell culture is characterized by a meat-like color. Each possibility represents a separate embodiment of the present invention.

According to certain embodiments, at least 60% of the cells further comprise exogenous iron or a salt thereof.

According to certain embodiments, the non-human-animal-derived cells of the cell culture comprise a combination of at least one natural colorant and vitamin B12. According to certain exemplary embodiments, the non-human-animal-derived cells of the cell culture comprise a combination of at least one natural colorant, vitamin B12 and iron or a salt thereof.

According to certain embodiments, at least 60% of the plurality of non-human-animal-derived cells comprises the at least one exogenous supplement. According to certain embodiments, at least 65%, 70%, 75%, 80% of the plurality of non-human-animal-derived cells comprises the at least one exogenous supplement. According to other embodiments, at least 85% of the plurality of non-human-animalderived cells comprises the at least one exogenous supplement. According to yet additional embodiments, 60-100% of the plurality of non-human-animal-derived cells comprise the at least one exogenous supplement. According to other embodiments, 60-90%, or 60-80% or 60-70% of the plurality of non-human-animal-derived cells comprise the at least one exogenous supplement.

According to certain embodiments, the present invention provides a non-human-animal derived cell comprising an exogenous supplement selected from the group consisting of at least one natural colorant, cobalamin (vitamin B12), and a combination thereof, wherein the non-human-animal-derived cell is characterized by a meat-like color. Each possibility represents a separate embodiment of the present invention.

According to certain embodiments, the non-human-animal derived cell further comprises iron or a salt thereof.

According to certain embodiments, the present invention provides a non-human-animal derived cell comprising an exogenous supplement selected from the group consisting of at least one natural colorant, cobalamin (vitamin B12), iron or a salt thereof, yeast extract and any combination thereof, wherein the non-human-animal-derived cell is characterized by a meat-like color. Each possibility represents a separate embodiment of the present invention.

According to certain embodiments, the present invention provides cultured meat comprising a plurality of non-human-animal derived cells, wherein the cells comprise at least one exogenous supplement selected from the group consisting of at least one natural colorant, cobalamin (vitamin B12), and a combination thereof, wherein the cultured meat is characterized by a meat-like color. According to some embodiments, the cultured meat comprises a plurality of non-human-animal derived cells, wherein the cells further comprise iron or a salt thereof. According to yet further embodiments, the cultured meat comprises a plurality of non-human-animal derived cells, wherein the cells comprise at least one exogenous supplement selected from the group consisting of at least one natural colorant, cobalamin (vitamin B12), iron or a salt thereof, yeast extract and any combination thereof, wherein the cultured meat is characterized by a meat-like color. According to certain exemplary embodiments, the plurality of non-human-animal derived cells forms the cultured meat. Each possibility represents a separate embodiment of the present invention.

According to certain embodiments, the color of the cell culture and/or of the cultured meat resembles the color of myoglobin. According to certain embodiments, the color of the cell culture and/or cultured meat resembles lean meat cut. According to certain embodiments, the color of the cell culture and/or cultured meat resembles slaughtered meat. According to certain embodiments, the color of the cell culture and/or cultured meat is brown. According to certain embodiments, the color of the cell culture and/or cultured meat is red to bright red. According to certain embodiments, the color of the cell culture and/or cultured meat is pink-purplish.

According to certain exemplary embodiments, the color of the cell culture and/or cultured meat varies in the range of brown to red.

According to certain embodiments, the non-human-animal-derived cells of the cell culture and/or the cultured meat further comprise an exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention.

According to certain embodiments, the vitamin D is selected from the group consisting of vitamin D3 and vitamin D2. Each possibility represents a separate embodiment of the present invention.

The profile of fatty acids that reaches the intestine in ruminant animals will be very different from what the animal has consumed. This is because of the extensive biohydrogenation that occurs in the rumen as a result of bacterial activity (Drackley, J. K. Overview of Fat Digestion and Metabolism in Dairy Cows; University of Illinois: Urbana, Ill., USA, 2007; pp. 1-9). Advantageously, the teachings of the present invention enable controlling the fatty acid profile taken up by the non-human-animal-derived cells, and accordingly provides for cultured meat and products thereof with a pre-set, desired fatty acid profile.

According to certain embodiments, the fatty acid is an unsaturated fatty acid selected from the group consisting of Omega 3 fatty acids, including, but not limited to, DHA, EPA and ALA; Omega 6 fatty acids, including, but not limited to LA, GLA, Calendic acid, and Arachidonic acid; Omega 9 fatty acids, including, but not limited to Erucic acid/cis-13-docosenoic acid, Oleic acid and Elaidic acid; and any combination thereof. According to certain embodiments, the fatty acid is a saturated acid. According to some embodiments, the saturated acid is stearic acid. Each possibility represents a separate embodiment of the present invention.

Stearic acid is a unique saturated fatty acid which, in contrast to other saturated fatty acids found in in food, which increase the concentration of cholesterol in the blood, has a different effect and does not cause an increase in blood fats.

According to certain embodiments, the non-human-animal-derived cells of the cell culture and/or the cultured meat further comprises at least two fatty acids.

One obstacle in introducing cultured meat products to the market is its appearance, as customers are looking for the familiar appearance of meat. The cultured non-human-animal-derived cells of the present invention comprise at least one of natural colorant and vitamin B12, which provide the cells with a color mimicking whole-animal derived meat. Furthermore, these specific coloring compounds has been selected due to their beneficial value to the consumers in addition to their color.

Meat color may be measured by several methods. The color of fresh animal-derived meat is determined mainly by the relative proportion of three meat pigments: purple reduced myoglobin (Mb), red oxymyoglobin (MbO$_2$) and brown metmyoglobin (MetMb). According to certain methods, ratio of the absorbance at 580 nm:630 nm is determined, wherein ratios above 1.0 indicate more redness (Strange, E D et al. 1974. Food Sci. 39:988-992). The second method is determining 650/570 nm ratio, wherein values of ≈1.1 indicates no cured color; ≈1.6 indicates moderate fade; ≈1.7 to 2.0 indicates noticeable cured color; and ≈2.2 to 2.6 indicate excellent cured color (Hunt, M. C., and D. H. Kropf. 1988. Unpublished data).

Alternative method is not based on absorbance at a certain wavelength but on measurement of tristimulus values, also referred to as CIE system. This is a colorimetric method which is designed to perform a type of psychophysical sample analysis by mimicking human eye-brain perception. The method is based on the three primary color receptors of the human eye quantified into coordinate values of L*a*b*. Larger ratios of a*/b* (or decreases in b*/a*) indicate more redness and less discoloration (Setser, C S. 1984. J. Food Qual. 6:183-197). L*: light vs. dark where a low number (0-50) indicates dark and a high number (51-100) indicates light.

a*: Red vs. green where a positive number indicates red and a negative number indicates green.

b*: Yellow vs. blue where a positive number indicates yellow and a negative number indicates blue.

The L*C*h color space is similar to L*a*b*, but it describes color differently, using cylindrical coordinates instead of rectangular coordinates.

In this color space, L* indicates lightness, C* represents chroma (color saturation), and h is the hue angle (0-360°).

C*: color saturation-scale 0-100. Higher value represents higher pigment amount in the sample.

h scale: hue angle (0-360°). h value around 0° (=360°) indicates red color; h value around 180° indicates blue.

Chroma and hue are calculated from a* and b* coordinates in L*a*b*. Deltas for lightness ($\Delta L^*$), chroma ($\Delta C^*$), and hue ($\Delta H^*$) may be positive (+) or negative (-). These are expressed as:

$\Delta L^*(L^*\text{sample minus } L^*\text{standard})$=difference in lightness and darkness: (+)=lighter,(-)=darker;

$\Delta C^*(C^*\text{sample minus } C^*\text{standard})$=difference in chroma: (+)=brighter,(-)=duller;

$\Delta H^*(H^*\text{sample minus } H^*\text{standard})$=difference in hue.

Any method for measuring the color of the non-human-animal-derived cell culture and/or cultured meat of the present invention as is known in the art can be used according to the teachings of the present invention.

According to certain embodiments, the cell culture comprises at least one compound having an absorbance at a wavelength or plurality of wavelengths of from about 300 nm to about 700 nm. Cobalamin (vitamin B12) absorbance peak is at 361 nm; beta carotene absorbance peaks are at 450 nm, 480 nm, and 520 nm; Lycopene absorbance peaks are at 360 nm, 443 nm, 471 nm, 502 nm; Canthaxanthin peak is at 480 nm.

Any method as is known in the art for measuring the spectral absorbance of the natural colorant pigments or the color-providing compounds can be used according to the teachings of the present invention.

According to some embodiments, the content of the coloring compound is measured by chemical reaction and/or HPLC and/or UPLC as is known in the art.

According to some embodiments, the pigments are first extracted from the cells and the absorbance of the pigment extract is measured by spectrophotometer. According to other embodiments, the absorbance of the pigment extract is measured by colorimeter.

According to certain exemplary embodiments, the natural colorant is a carotenoid.

According to certain exemplary embodiments, the carotenoid providing the color to the non-human-animal-derived cell culture and/or cultured meat according to the teachings of the present invention is selected from the group consisting of α-carotene, β-carotene, lycopene, cryptomonaxanthin, alloxanthin, zeaxanthin, violaxanthin, α-zetcarotene, lycopersene, hexahydrolycopene, torulene, cynthiaxanthin, pectenoxanthin, crustaxanthin, gazaniaxanthin, OH-chlorobactene, loroxanthin, lutein, lycoxanthin, rhodopin, rhodopinol (warmingol), saproxanthin, oscillaxanthin, phleixanthophyll, rhodovibrin, spheroidene, diadinoxanthin, luteoxanthin, mutatoxanthin, citroxanthin, zeaxanthin furanoxide, neochrome, foliachrome, trollichrome, vaucheriaxanthin, rhodopinal, warmingone, torularhodinaldehyde, torularhodin, torularhodin methyl ester, astacene, astaxanthin, canthaxanthin (aphanicin), chlorellaxanthin, capsanthin, capsorubin, cryptocapsin, 2,2'-diketospirilloxanthin, echinenone, 3'-hydroxyechinenone, flexixanthin, 3-OH-canthaxanthin (adonirubin, phoenicoxanthin), hydroxyspheriodenone, okenone, pectenolone, phoeniconone (dehydroadonirubin), phoenicopterone, rubixanthone, sphonaxanthin, astacein, fucoxanthin, isofucoxanthin, physalien, siphonein, β-apo-2'-carotenal, apo-2-lycopenal, apo-6'-lycopenal, azafrinaldehyde, bixin, citranaxanthin, crocetin, crocetinsemialdehyde, crocin, hopkinsiaxanthin, methyl apo-6'-lycopenoate, paracentrone, sintaxanthin, actinioerythrin, peridinin, pyrrhoxanthininol, semi-α-carotenone, semi-3-carotenone, triphasiaxanthin, retro-carotenoids and retro-apo-carotenoids, eschscholtzxanthin, eschscholtzxanthone, rhodoxanthin, tangeraxanthin, nonaprenoxanthin, decaprenoxanthin, C.p. 450 2-[4-hydroxy-3-(hydroxymethyl)-2-butenyl]-2'-(3-methyl-2-butenyl)-b, b-carotene, C.p. 473 2'-(4-hydroxy-3-methyl-2-butenyl)-2-(3-methyl-2-butenyl)-3',4'-didehydro-1',2'-dihydro-b,y-caroten-1'-ol, and bacterioruberin. Each possibility represents a separate embodiment of the present invention.

According to certain embodiments, the carotenoid is selected from the group consisting of beta-carotene, lycopene, canthaxanthin, bixin, betalain and any combination thereof. Each possibility represents a separate embodiment of the present invention.

According to certain embodiments, the carotenoid is the carotene lycopene.

Lycopene is a natural red pigment molecule with established antioxidant properties. Synthetic lycopene as well as lycopene obtained from natural source have been reported to be safe (Generally Recognized as Safe, GRAS) by the U.S. FDA when used as food supplement in various food products, at levels ranging from 0.5 to 7%. In safety studies, no adverse effects were observed at intake levels up to 3 g/(kg*d) of dietary or formulated lycopene (Trumbo, P. R. J. Nutr. 2005, 135, 2060S-2061S).

According to certain embodiments, the non-human-animal-derived cell culture comprise a plurality of cells providing for an amount of lycopene of from about 0.1 mg/100 g cells to about 50 mg/100 g cells. According to some embodiments, the lycopene is in amount of from 1 mg/100 g cells to about 20 mg/100 g cells.

According to certain embodiments, the carotenoid is the xanthophyll canthaxanthin.

Canthaxanthin is a red-orange carotenoid that belongs to the xanthophyll group. This naturally occurring pigment is present in bacteria, algae and some fungi. Canthaxanthin is also responsible for the color of flamingo feathers, koi carp skin and crustacean shells. Canthaxanthin is widely used in poultry (broiler, laying hens) as a feed additive. It is added to animal feed to improve the color of chicken skins, egg yolks, salmon, and trout. Synthetic canthaxanthin is a nature-identical compound. The synthetic compound gives animal-derived food its characteristic red-orange hue. The size, shape or conformation of carotenoids also play key roles in their coloring properties. In addition, carotenoid-protein interactions are responsible for a wide range of red colors of canthaxanthin. (Esatbeyoglu, T., & Rimbach, G. 2016. Molecular Nutrition & Food Research, 61(6), 1600469. doi:10.1002/mnfr.201600469). The recommended upper dose of canthaxanthin according to the U.S. Food and Drug Administration is 30 milligrams per pound of solid or semisolid food or per pint of liquid food.

According to certain embodiments, the non-human-animal-derived cell culture comprise a plurality of cells providing for an amount of canthaxanthin of from about 1 mg/100 g cells to about 100 mg/100 g cells. According to some embodiments, the canthaxanthin is in amount of from 10 mg/100 g cells to about 50 mg/100 g cells.

According to certain embodiments, the carotenoid is the carotene beta-carotene.

Beta-Carotene (or β-carotene) is an isoprenoid compound which is not synthesized in animals but bio-synthesized by plants and micro-organisms. Beta-carotene, serve as an important source of vitamin A, the major known function of carotenoids in humans. According to published FDA information on Apr. 20, 2012, β-Carotene is affirmed as GRAS. It may be used as a nutrient supplement or a color additive. The use of β-Carotene as an antioxidant nutrient is also allowed.

Vitamin A has an equation: 1 µg of retinol=6 µg beta-carotene. Recommended upper limit of Vitamin A is 3 mg/day, which means 18 mg/day of beta-carotene.

In addition, intake of >30 mg of beta-carotene daily may lead to hypercarotenemia which is characterized by a yellowish coloration of the skin (including soles of feet and palms of hand). This is harmless and reversible (Mason, P. 2001. Dietary Supplements. Pharmaceutical press, London).

According to certain embodiments, the non-human-animal-derived cell culture comprise a plurality of cells providing for an amount of beta-carotene of from about 1 mg/100 g cells to about 100 mg/100 g cells. According to some embodiments, the beta-carotene is in amount of from 10 mg/100 g cells to about 50 mg/100 g cells.

As is exemplified in the Example section hereinbelow, the cells were loaded with medium enriched with an exogenous supplement selected from the group consisting of beta-carotene, lycopene, canthaxanthin, and/or Vitamin B12, affecting both color and nutritional values of the cells. The enriched cells provide beneficial amount of said nutrients.

According to some embodiments, the carotenoid is bixin.

Bixin, another member of the carotenoid family, found in annatto, is a natural food coloring obtained from the seeds of the tropical plant achiote tree (*Bixa orellana*). Achiote seeds and the extracts obtained from them have been used for more than 200 years in Europe and North America as food colorants, giving a red-orange-yellow coloring to food products (Smith, J and Wallin, H. 2006. Annatto Extracts: Chemical and Technical Assessment). Nowadays, bixin occupies the second place among the main natural colors used worldwide (Giridhar P. and Parimalan R A. Asia Pac J Mol Biol Biotechnol. 2010. 18:77-79; Chuyen H V and Hoi N T. Eun J B. Int J Food Sci Tech. 2012. 47:1333-1338). Both color supplements are approved for use by both the FDA and the European Food Safety Authority (EFSA).

According to additional certain exemplary embodiments, the natural colorant is at least one betalain. According to some embodiment, the betalain is selected from the group consisting of betacyanin and betaxanthins. According to some embodiments, the betacyanin is selected from the group consisting of betanin, isobetanin, probetanin, and neobetanin. According to some embodiments, the betaxanthin is selected from the group consisting of vulgaxanthin, miraxanthin, portulaxanthin, and indicaxanthin.

According to certain embodiments, the non-human-animal-derived cell culture comprise a plurality of cells providing for an amount of betalain of from about 0.1 mg/100 gr cells to about 600 mg/100 gr cells of the at least one betalain.

Betalains are a class of red and yellow indole-derived pigments found in plants of the Caryophyllales, where they replace anthocyanin pigments. There are two categories of betalains: betacyanins, having reddish to violet color, including betanin, isobetanin, probetanin, and neobetanin; and betaxanthins with yellow to orange color, including vulgaxanthin, miraxanthin, portulaxanthin, and indicaxanthin. Betalains are commonly used as food colorants, particularly the beet-derived betanin. Recently, it has been suggested that betanin also has health benefits as antioxidant.

As described hereinabove, vitamin B12 is an essential vitamin, which, as carotenoids, is not synthesized by the human body and obtained by consuming animal-derived products. The cobalt forming part of the vitamin B12 structure gives its distinct red color, and thus vitamin B12 has a dual function as a colorant and as an essential vitamin according to the teachings of the present invention.

The U.S. Institute of Medicine (TOM, now the Health and Medicine Division (HMD)) updated Estimated Average Requirements (EARs) and Recommended Dietary Allowances (RDAs) for vitamin B12 in 1998. The current EAR for vitamin B12 for women and men ages 14 and up is 2.0 µg/day; the RDA is 2.4 µg/day.

EFSA refers to the collective set of information as Dietary Reference Values. For women and men over age 18 the Adequate Intake (AI) of vitamin B12 is set at 4.0 µg/day. AI for pregnant women is 4.5 µg/day, and for lactating women 5.0 µg/day. For children aged 1-17 years the AIs increase with age from 1.5 to 3.5 µg/day.

The EFSA and IOM have however decoded that there is no sufficient evidence which require setting a Tolerable Upper Intake Levels (UL) for vitamin B12.

The present invention now shows that incubating bovine-embryonic fibroblasts and myoblasts in growth medium containing 1 mg of cyanocobalamin per ml resulted in an amount of the vitamin which gives the cells distinct red-pink color.

Furthermore, the present invention shows that bovine-derived cells are capable of linear uptake of Vitamin B12 from the medium at the concentration examined, reaching amounts of from about 10 mg/100 g cells to about 100 mg/100 g cells.

Iron is an essential micronutrient that ensures the development of normal red blood cells and healthy immune function. Iron deficiency may result in anemia and has been shown to negatively affect child development. The absorption of dietary iron is a variable and dynamic process. The amount of iron absorbed compared to the amount ingested is typically low, but may range from 5% to as much as 35%, depending on circumstances and type of iron. The best-absorbed forms of iron come from animal products. Absorption of iron from animal products, and some plant products, is in the form of heme iron, and is more efficient allowing absorption of from 15% to 35% of the intake. Heme iron in animals is from blood and muscle and heme-containing proteins in meat and mitochondria. The cultured meat of the present invention comprises cells fortified with iron which improve the nutritional value of the cultured meat.

According to certain embodiments, the non-human-animal-derived cell culture comprise a plurality of cells providing for an amount of iron or a salt thereof of from about 0.01 mg/100 gr cells to about 50 mg/100 gr cells. According to certain embodiments, the iron is in an amount of from about 0.1 mg/100 gr cells to about 40 mg/100 gr cells. According to certain embodiments, the iron amount is from about 0.5 mg/100 gr cells to about 5 mg/100 gr cells.

According to certain embodiments, the non-human-animal-derived cells of the cultured meat further comprise an exogenous supplement selected from the group consisting of folate (vitamin B9), zinc and/or a salt thereof, selenium and/or a salt thereof, vitamin D, vitamin E, Coenzyme Q10, at least one unsaturated fatty acid, at least one saturated fatty acid, and any combination thereof. Each possibility represents a separate embodiment of the present invention.

Coenzyme Q10, also known as ubiquinone, ubidecarenone, coenzyme Q, and abbreviated at times to CoQ10, CoQ, or Q10, is a coenzyme. This fat-soluble substance, which resembles a vitamin, is present in all respiring eukaryotic cells, primarily in the mitochondria. It is a component of the electron transport chain and participates in aerobic cellular respiration, which generates energy in the form of ATP. CoQ10 is sold as a dietary supplement. There is no established ideal dosage of CoQ10; a typical daily dose is 100-200 milligrams. CoQ10 is a crystalline powder insoluble in water. The CoQ10 can be modified in several methods in order to increase its absorption by increasing its solubility in water.

According to certain embodiments, the non-human-animal-derived cells further comprise Coenzyme Q10. According to certain embodiments, the non-human animal-derived cell culture comprise a plurality of cells providing for Coenzyme Q10 in an amount of from about 0.5 mg/100 gr cells to about 20 mg/100 gr cells.

According to certain embodiments, the non-human-animal-derived cells further comprise folate. According to certain embodiments, the non-human animal-derived cell culture comprise a plurality of cells providing for an amount of folate of from about 50 µg/100 gr cells to about 500 µg/100 gr cells.

According to certain embodiments, the non-human-animal-derived cells further comprise vitamin E. According to certain embodiments, the non-human animal-derived cell culture comprise a plurality of cells providing for vitamin E amount of from about 0.5 mg/100 gr cells to about 50 mg/100 gr cells. According to certain embodiments, the plurality of cells provides for vitamin E amount of from about 1mg/100 g cells to about 10 mg/100 g cells.

According to certain embodiments, the non-human-animal-derived cells further comprise selenium and/or a salt thereof. According to certain embodiments, the non-human animal-derived cell culture comprise a plurality of cells providing for an amount of selenium of from about 5.0 µg/100 gr cells to about 60 µg/100 gr cells.

According to certain embodiments, the non-human-animal-derived cells further comprise vitamin D. According to certain embodiments, the non-human-animal-derived cell culture comprise a plurality of cells providing for Vitamin D in an amount of from about 0.01 µg/100 gr cells to about 150 µg/100 gr cells. According to certain embodiments, the vitamin D amount is from about 0.1 µg/100 gr cells to about 100 µg/100 gr cells. According to certain embodiments, the vitamin D amount is from about 0.1 µg/100 gr cells to about 15 µg/100 gr cells.

According to certain embodiments, the non-human-animal-derived cells further comprise at least one unsaturated fatty acid. According to certain embodiments, the non-human-animal-derived cell culture comprise a plurality of cells providing for unsaturated fatty acid in an amount of from about 5 mg/100 gr cells to about 2500 mg/100 gr cells. According to certain embodiments, the amount of the at least one unsaturated fatty acid is from about 5 mg/100 gr cells to about 1500 mg/100 gr cells. According to certain embodiments, the amount of the at least one unsaturated fatty acid is of from about 5 mg/100 gr cells to about 500 mg/100 gr cells. According to certain embodiments, the amount of the at least one unsaturated fatty acid is of from about 5 mg/100 gr cells to about 50 mg/100 gr cells.

According to certain embodiments, the non-human-animal-derived cells of the cultured meat comprise at least one natural colorant selected from the group consisting of lycopene, canthaxanthin and a combination thereof; vitamin B12; iron or a salt thereof; at least two fatty acids; selenium and/or a salt thereof; zinc and/or a salt thereof; vitamin E, Coenzyme Q10, and vitamin D.

According to yet another aspect, the present invention provides an enriched cell-culture liquid medium for growing non-human-animal-derived cells, the medium comprising at least one supplement selected from the group consisting of at least one natural colorant, cyanocobalamin (vitamin B12) and a combination thereof, wherein the supplement is in amount sufficient to confer meat-like color to a the non-human-animal derived cells.

According to certain embodiments, the enriched cell-culture liquid medium is characterized by having absorbance at a plurality of wavelengths between about 300 and about 700 nm. Cyanocobalamin (vitamin B12) peak absorbance is at 361 nm; Carotenes peaks absorbance: beta carotene: 450, 480, 520 nm; Lycopene peaks 360, 443, 471, 502 nm. Bixin 360, 470-476, 501-507 nm; Betanin peak absorbance is at 535 nm Canthaxanthin peak 480 nm.

According to yet another aspect, the present invention provides an enriched cell-culture liquid medium for producing cultured meat having meat-like color, the medium comprising a combination of exogenous supplements comprising at least one natural colorant and cyanocobalamin (vitamin B12).

According to certain embodiments, the present invention provides an enriched cell-culture liquid medium for producing cultured meat having meat-like color, the medium comprising a combination of exogenous supplements comprising at least one natural colorant, cyanocobalamin (vitamin B12) and iron or a salt thereof. According to certain embodiments, the medium comprises a combination of exogenous supplements consisting of at least one colorant, B12 and iron or a salt thereof.

In addition to the need for appealing appearance of cultured meat product, taste is of significant importance. Taste of the cultured meat may be improved by the addition of natural or synthetic flavors. Yeast extracts are known in the food industry as flavor precursors, and are typically added to give meat bouillon taste to non-meat dishes. The present invention now discloses that, unexpectedly, culturing non-human-animal derived cells in medium containing yeast extract results in cultured cells that form food product having improved, meat-like taste.

According to certain embodiments, the medium comprises a supplement composition comprising at least one colorant, B12 and yeast extract. According to certain embodiments, the medium comprises a supplement composition consisting of at least one colorant, B12 and yeast extract.

According to certain embodiments, the medium comprises a supplement composition comprising at least one colorant, B12, iron or a salt thereof and yeast extract. According to certain embodiments, the medium comprises a supplement composition consisting of at least one colorant, B12, iron or a salt thereof and yeast extract.

According to yet another aspect, the present invention provides an enriched, liquid cell-culture medium for producing cultured meat having meat-like color, the medium comprising a supplement selected from the group consisting of at least one natural colorant, cyanocobalamin (vitamin B12), iron or a salt thereof and any combination thereof, wherein the supplement is in amount sufficient to confer meat-like color to the cultured meat.

According to yet another aspect, the present invention provides an enriched, cell-culture liquid medium for producing cultured meat having meat-like color, the medium comprising a supplement selected from the group consisting of at least one natural colorant, cyanocobalamin (vitamin B12), iron or a salt thereof, yeast extract and any combination thereof, wherein the supplement is in amount sufficient to confer meat-like color to the cultured meat.

According to some embodiments, the enriched medium further comprising at least one supplement selected from the group consisting of folate, zinc and/or a salt thereof, selenium and/or a salt thereof, vitamin D, vitamin E, Coenzyme Q10, at least one unsaturated fatty acid, at least one saturated fatty acid and any combination thereof. Each possibility represents a separate embodiment of the present invention.

According to certain embodiments, the medium comprises a supplement composition comprising at least one colorant, B12 and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention. According to certain embodiments, the medium comprises a supplement composition consisting of at least one colorant, B12 and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention.

According to certain embodiments, the medium comprises a supplement composition comprising at least one colorant, B12, iron or a salt thereof and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention. According to certain embodiments, the medium comprises a supplement composition consisting of at least one colorant, B12, iron or a salt thereof and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention.

According to certain embodiments, the medium comprises a supplement composition comprising at least one colorant, B12, yeast extract and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention. According to certain embodiments, the medium comprises a supplement composition consisting of at least one colorant, B12, yeast extract and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention.

According to certain embodiments, the medium comprises a supplement composition comprising at least one colorant, B12, iron or a salt thereof, yeast extract and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention. According to certain embodiments, the medium comprises a supplement composition consisting of at least one colorant, B12, iron or a salt thereof, yeast extract and at least one exogenous supplement selected from the group consisting of folate (vitamin B9), zinc and/or a salt thereof, selenium and/or a salt thereof, vitamin D, vitamin E, Coenzyme Q10, at least one fatty acid, and any combination thereof. Each possibility represents a separate embodiment of the present invention.

According to some embodiments, the enriched medium comprises the folate at a concentration of from about 100 µg/ml to about 5 mg/ml.

According to some embodiments, the enriched medium comprises the selenium and/or a salt thereof at a concentration of from about 5 ng/ml to about 500 ng/ml.

According to some embodiments, the enriched medium comprises the vitamin D at a concentration of from about 0.1 pM to about 100 µM. According to certain exemplary embodiments, the enriched medium comprises the vitamin D at a concentration of from about 0.1 nM to about 1 µM.

According to some embodiments, the enriched medium comprises the vitamin E at a concentration of from about 10 nM to about 250 µM.

According to some embodiments, the enriched medium comprises the at least one unsaturated fatty acid at a concentration of from about 10 µM to about 350 µM.

According to some embodiments, the enriched medium comprises the Coenzyme Q10 at a concentration of from about 5 µg/ml to about 2 mg/ml.

Antimicrobial peptides (AMPs) are diverse group of natural proteins present in animals, plants, insects and bacteria. These peptides are part of the defense mechanism of a host from pathogenic organisms and have been found to be an alternative to chemical preservatives.

According to certain embodiments, the medium of the present invention further comprises AMPs preventing contamination of the cultured cells. As described hereinabove, these peptides are natural preservatives. AMPs are produced by bacteria present in many types of food since ancient times, such as cheeses, yogurts, and Portuguese fermented meat, and have been shown to be safe for human consumption, and thus approved for use in the food industry.

A commonly used AMP is nicin, a peptide having 3.5 KDa molecular weight, 34 amino acids, positive charge and antimicrobial activity against gram-positive bacteria including *Bacilluses, Micrococcuses, Staphylococcrus aureuses, Listeria monocytogenes* and *Clostridiums*, and low antimicrobial activity against gram-negative bacteria. Nicin is used for protecting and increasing preservation time of pasteurized cheeses, dairy desserts, canned food, salted meat and sea food. (Thomas L. V. and Delves-Broughton, J. 2005. In: Davidson M P et al., Antimicrobial in foods, Third Edition, Published by CRC Press, pp. 237-274). Although nicin is in use in the food industry for several decades, no development of resistant food-spoilage organisms has been detected.

Anthocyanins are colored water-soluble pigments belonging to the phenols' group. Below pH 3, anthocyanin solutions display their most intense red coloration. When the pH of such solutions is raised, their red color normally fades to the point where they appear colorless in the pH range of 4 to 5. Further increases in pH give rise to anthocyanin solutions which are purple and blue, which, upon storage or heat treatment, have been observed to change in pigmentation from blue to yellow. Acylated and co-pigmentated anthocyanidins have higher heat stability, thus maintain the structure even in different pH conditions. Anthocyanins are the value-added colorants that can be used for preventing several diseases, including cardiovascular disease, cancers, diabetes, some metabolic diseases, and microbial infection. These compounds also improve visual ability and have neuroprotective effect. (Khoo, H E et al. 2017. Food Nutr. Res. 61:1361779).

According to yet additional aspect, the present invention provides a method for producing cultured meat characterized by meat-like color, the method comprising culturing non-human-animal derived cells in the enriched cell-culture medium of the present invention.

Culturing the non-human-animal-derived cell in the medium of the invention can be performed at any stage of the cultured meat production. According to certain embodiments, adding the enriched medium of the invention at times of low cell-division rate, as to obtain a more intense, slaughtered-meat like color, may be preferable. According to certain embodiments, the enriched medium of the present invention is added to non-human-animal-derived cells forming a meat culture towards the end of the culture growth. According to certain exemplary embodiments, the medium is added to cells having substantially constant glucose uptake rate (GUR). According to some embodiments, the enriched medium is added to the cell from about 1 day to about 3 days before culturing is completed.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

UPLA-UV/Vis Carotene Analyses

Beta-carotene, Lycopene and Canthaxanthin were analyzed by UPLC-UV/Vis instrument by Analyst Research Laboratories under the following conditions:
  Instrument: Waters ACQUITY UPLC system
  Column: Phenomenex Kinetex 2.6 pm Cis 100×2. 1 mm; part no. OOD-4462-AN
  Column temperature: 50° C.
  Auto sampler temp.: 5° C.
  Detector: Photodiode array wavelength range 250-499 nm
  Resolution: 3.6 nm
  Sample rate: 10 points/second
  Mobile phase A: Acetonitrile:methanol:ammonium acetate buffer 25:25:50
  Mobile phase B: Acetonitrile:methanol:dichloromethane: hexane 70:25:2.5:2.5
  Flow: 0.5 mL/minute
  Injection volume: 17 pL partial loop with needle overfill
  Weak wash volume: 600 μL
  Strong solvent volume: 200 μL
  Seal wash: 1 minute
  Run time: 8 minutes
  Next injection delay: 5 minutes
  The gradient conditions are presented in Table 1 hereinbelow.

TABLE 1

| UPLC gradient table | | | |
| Time (min) | % A | % B | Curve |
| --- | --- | --- | --- |
| 0 | 100 | 0 | — |
| 0.2 | 100 | 0 | 6 |
| 4 | 0 | 100 | 6 |
| 7.9 | 0 | 100 | 6 |
| 8 | 100 | 0 | 6 |

Sample and Control Sample Solution Preparation

Beta-carotene, Lycopene or Canthaxanthin were prepared in one replicate as follows:

100 mg sample/control sample was transferred into a polypropylene vial suitable for homogenization. 100 mg/1 mm glass beads were added, followed by 2 mL reconstitution solution. Samples were homogenized for 30 seconds to disrupt the cells. The supernatant was transferred to UPLC vials for analysis after centrifugation of the vials using UPLC-UV/Vis.

Spiked Control Sample Solution Preparation

Samples were prepared in one replicate as follows:

100 mg control sample was transferred into a polypropylene vial suitable for homogenization. 100 mg/1 mm glass beads were added, followed by 2 mL standard solution. Samples were homogenized for 30 seconds to disrupt the cells. The supernatant was transferred to UPLC vials for analysis after centrifugation of the vials.

Quantitation of Carotenoids in Samples

The carotenoid content in the samples of Beta-carotene, Lycopene and Canthaxanthin was determined by single point calibration against the "standard" solution prepared from each carotenoid separately. The peak areas for each carotenoid were determined at the wavelengths of the peak maxima.

HPLC-UV/Vis

BEF cells were exposed to different concentration of vitamin B12 for 24 hours. The cells pellet was analyzed by HPLC.

Analytical Method:

The analyses were performed by HPLC using the following conditions:

HPLC-UV/Vis Operations Conditions
  Instrument: Agilent 1100 system
  Column: Waters Symmetry 5 nm C18 150×4.6 mm
  Column temperature: 30° C.
  Autosampler temp: 5° C.
  Detector: UV at 361 nm
  Mobile phase A: 0.025% TFA in Water
  Mobile phase B: Acetonitrile
  Flow: 1.0 mL/minute
  Injection volume: 100 μl
  Run time: 30 minutes Gradient conditions are presented in Table 2 hereinbelow.

TABLE 2

| HPLC gradient table | | |
| Time (min) | % A | % B |
| --- | --- | --- |
| 0 | 95 | 5 |

TABLE 2-continued

HPLC gradient table

| Time (min) | % A | % B |
|---|---|---|
| 1 | 95 | 5 |
| 20 | 5 | 95 |
| 25 | 5 | 95 |
| 25.1 | 95 | 5 |
| 30 | 95 | 5 |

Standard Stock Solution Preparation

Standard stock solutions were prepared in duplicate as follows:

10 mg of Vitamin B12 V2876 reference material were transferred into a 20 mL amber volumetric flask, completed to volume with HPLC water and mixed.

Working Standard Solution Preparation:

Working standards were prepared in duplicate as follows:

1 mL of standard stock solution was transferred into a 50 mL amber volumetric flask, completed to volume with HPLC water and mixed.

Sample and Control Sample Solution Preparation

Samples were prepared in one replicate as follows:

50 mg sample/control were transferred into a polypropylene vial suitable for the homogenizer. 50 mg 1 mm glass beads were added, followed by 2 mL diluent (water).

Samples were homogenized for 30 seconds to disrupt the cells. The supernatant was transferred to HPLC vials for analysis after centrifugation of the vials.

Spiked Control Sample Solution Preparation

Samples were prepared in one replicate as follows:

50 mg control Sample were transferred into a polypropylene vial suitable for the homogenizer.

50 mg 1 mm glass beads were added, followed by 2 mL working standard solution.

Samples were homogenized for 30 seconds to disrupt the cells. The supernatant was transferred to HPLC vials for analysis after centrifugation of the vials.

Quantitation of Vitamin B12 in Samples

The Vitamin B12 content in the samples was determined by single point calibration against the working standard solution.

Spiking Recovery for Control Samples Spiked with Vitamin B12

| Vitamin B12 spiked | Spiking recovery (%) |
|---|---|
| B12 | 98 |

Cells

BEF—Culture of bovine embryonic fibroblasts derived from embryonic skeletal muscle tissue. 90%-100% of the cells in the culture are BEFs.

BEM—Culture of bovine embryonic myoblasts derived from embryonic skeletal muscle tissue.

BCL—Culture of fibroblasts derived from bovine umbilical cord lining.

Example 1: Use of Beta-Carotene for Coloring Bovine-Derived Cells

Bovine embryonic fibroblasts (BEF) were tested for their uptake of color compounds. The natural color of the bovine cells is white to yellow. Beta-carotene is a pro-vitamin-A that can be converted to vitamin A by the human body. Beta carotene has yellow-orange-red color.

Figure 1B:
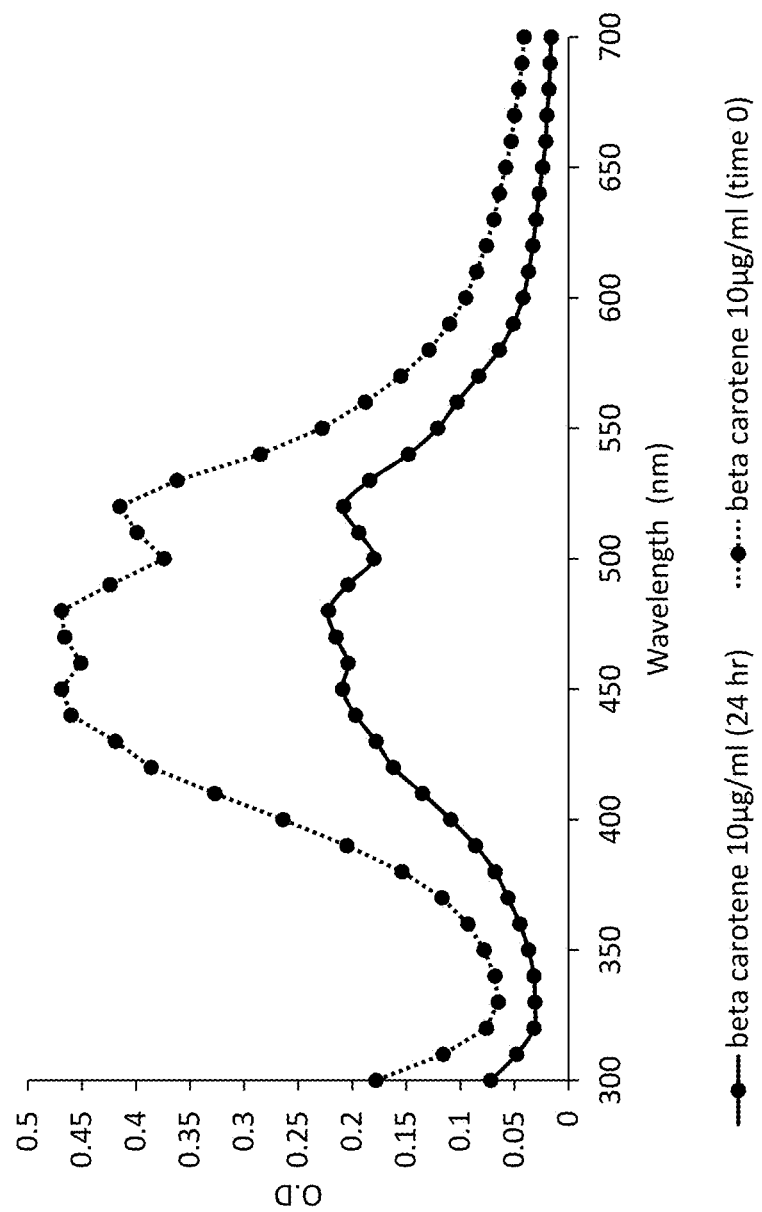
FIG. 1B: initial concentration of 10 µg beta-carotene per ml growth medium.

In one experiment, water soluble beta-carotene was added to $1.2*10^6$ cells in standard medium (DMEM, 10% FCS and 1% Penicillin/Streptomycin). The bovine cells were incubated at 38.5° C. 5% $CO_2$ with three concentrations of water-soluble beta-carotene: 1, 10 and 100 µg/ml. 24 hours after the addition of beta-carotene the cells were harvested by trypsinization (cells concentration after 24 hours was $1.4*10^6$ cells/ml). The cells were washed and re-suspended in PBS. Beta-carotene content was evaluated by analyzing the absorbance spectrum (at 300-700 nm) of the medium from which the cells were removed as well as of the harvested cells by spectrophotometer. FIG. 1 demonstrates beta-carotene uptake from the medium into bovine cells. The optical density of beta carotene in the growth medium as a result of the presence of bovine cells has changed over 24 hours of incubation. The peaks at 450, 480, and 520 nm were decreased by 2.7, 2.3 and 2.4-fold respectively after 24 hours. The decrease of beta carotene in the medium reflects an increase in its amount within or adhered to the cells which appeared to have strong orange color. Applying 100 µg of beta-carotene to $1.4*10^6$ cells results in a total uptake of 40 µg beta carotene by the cells.

In additional experiment, BEF cells were incubated with beta-carotene 10% emulsion red (DSM, Cat #5012538004) in standard medium (DMEM High Glucose, 10% FCS, 1% Pen-Strep) at a final beta carotene concentration of 110 µg/ml for 24 hours at 38° C., 5% $CO_2$.

The cells were then harvested by trypsinization and the pellet was washed three times with PBS. Cells pellet color was orange. $63*10^6$ cells (weighting 316 mg) were analyzed in UPLC method as described hereinabove. The quantitation of the amounts of carotenoids in the cells was performed by comparing said sample to the reference beta-carotene 10% emulsion red.

As can be seen in table 4 hereinbelow, applying 0.11 mg/ml beta-carotene to the cells resulted in uptake of 200 µg beta-carotene/gr cells. It is to be noted that beta-carotene in an emulsion form provides the cells with a red-orange color, compared to orange color of the cells resulting from uptake of water-soluble beta-carotene. Therefore, use of beta-carotene in an emulsion form is advantageous according to the teachings of the present invention.

Example 2: Iron Uptake

Use of Ferrous Bisglycinate for Coloring Bovine-Derived Cells

Ferrous bisglycinate is a water-soluble compound having dark brown color. Ferrous bisglycinate uptake by bovine fibroblasts derived from BCL cells was examined as described above for beta-carotene at three concentrations: 1500 µg/ml, 750 µg/ml and 375 µg/ml.

Figure 2:
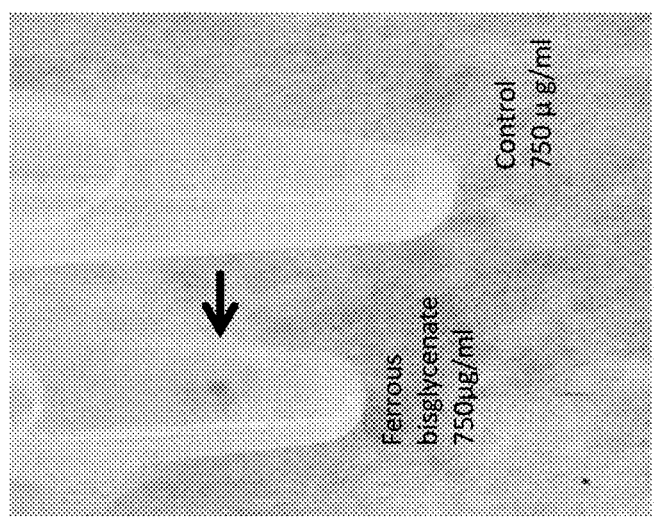
FIG. 2 shows accumulation of ferrous bisglycinate within bovine cells incubated for 24 hours in a medium containing 750 µg ferrous bisglycinate per ml growth medium.

Ferrous bisglycinate at a concentration of 1500 µg/ml was found to be toxic to the bovine cells. At 750 µg/ml concentration, the cells were colored to a light brown color (FIG. 2). 375 µg/ml did not color the cells.

Use of Iron for the Enrichment of Bovine Derived Cells

BEF cells at full confluence were incubated with Iron (II) Sulfate heptahydrate (Sigma, Cat #F8633) dissolved in standard medium (DMEM High Glucose, 10% FCS, 1% Pen-Strep) to final concentrations of 0.5 mM, for 24 hours at 38° C., 5% $CO_2$.

The cells were then harvested by trypsinization and the pellets were washed three times with PBS. Cells in weight of 1107 mg were analyzed using ICP-MS method.

Inductively coupled plasma-mass spectrometry (ICP-MS) is a powerful tool for analyzing trace metals in environmental samples. It is applicable to the determination of sub-μg/L concentrations of a large number of elements in water samples. The method measures ions produced by a radio-frequency inductively coupled plasma. Analyte species in liquid are nebulized and the resulting aerosol is transported by argon gas into the plasma torch. The ions produced by high temperatures are entrained in the plasma gas and introduced, by means of an interface, into a mass spectrometer. The ions produced in the plasma are sorted according to their mass-to-charge (m/z) ratios and quantified with a channel electron multiplier (Method 6020b Inductively Coupled Plasma-Mass Spectrometry published by US EPA).

BEF cells incubated with the standard medium only contained 8.36 μg iron/g cells, while incubating the cells in a medium supplemented with Iron Sulfate heptahydrate as described above resulted in cells containing 25.11 μg iron/g cells, an increase of about 3 fold.

Example 3: Cyanocobalamin Uptake

Use of Cyanocobalamin for Coloring Bovine-Derived Cells

Cyanocobalamin (Cbl) is a water-soluble vitamin B12, which has a red color. Cyanocobalamin uptake by BEF cells was examined as described above for beta-carotene at three concentrations: 1000, 100 and 10 μg/ml, and an incubation time of 24 h.

Figure 3:
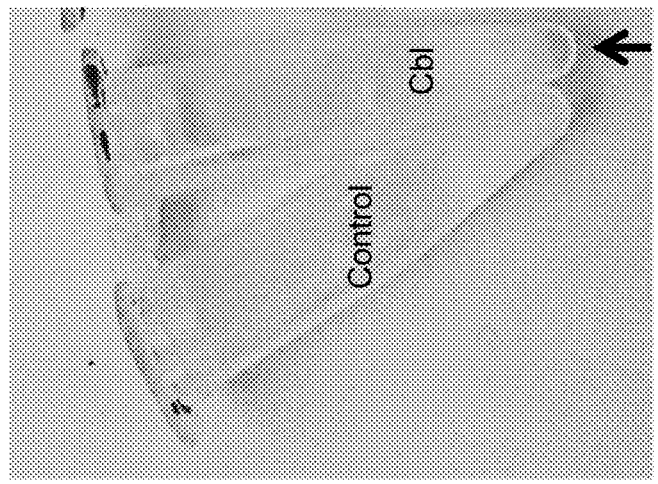
FIG. 3 shows accumulation of Cyanocobalamin (Cbl) within bovine cells incubated for 24 hours in a medium containing 1000 µg Cyanocobalamin (Cbl) per ml growth medium.

The cells were colored in red-pink when exposed to high concentration of 1000 μg/ml (FIG. 3). At 100 μg/ml and 10 μg/ml, there was no visual change in bovine cell color.

Use of Cyanocobalamin for the Enrichment of Bovine Derived Cells

Fully confluent BEF cells were incubated with Vitamin B12 (cyanocobalamin, Sigma, Cat #V2876) in standard medium (DMEM High Glucose, 10% FCS, 1% Pen-Strep) to final concentrations of: 13.3, 6.67, 3.33 and 1.67 mg/ml for 24 hours at 38° C., 5% $CO_2$.

The cells were then harvested by trypsinization and the pellet was washed three times with PBS. Cells pellets color was red-pink in various intensities, depending on the concentration of Vitamin B12. $12.8*10^7$ cells (weighting 764 mg) were transferred to analysis in HPLC method as described hereinabove. The quantitation of the amounts of Vitamin B12 in the cells was performed by comparing the sample to the reference-Vitamin B12.

As can be seen in table 3, applying 1.67, 3.33, 6.67 and 13.3 mg/ml vitamin B12 to the cells resulted in a linear uptake.

TABLE 3

Vitamin B12 Concentrations

| Vitamin B12 Concentration in the medium (mg/ml) | μg Vitamin B12/g cells |
|---|---|
| 1.67 | 104.0 |
| 3.33 | 417 |
| 6.67 | 851 |
| 13.33 | 1102 |

Example 4: Use of Zinc for the Enrichment of Bovine Derived Cells

A mixture containing BEF and BEM cells (with the majority being BEF cells) at full confluence were incubated with Zinc chloride (Sigma, Cat #Z0152) dissolved in standard medium (DMEM High Glucose, 10% FCS, 1% Pen-Strep) to a final concentration of 100 μM (13 μg/ml), for 72 hours at 38° C., 5% $CO_2$. The cells were then harvested by trypsinization and the pellet was washed three times with PBS. $17.8*10^7$ cells (weighting 1200 mg) were analyzed by/using IPC-MS method.

Cells incubated in the standard medium not supplemented with Zinc Chloride contained only 8.5 μg zinc/gr cells. Applying 100 μM zinc chloride to the cells resulted in uptake of 30.44 μg zinc/gr cells, i.e. increase of about 3.6 folds.

Example 5: Omega 3 and Omega 9

Cis-4,7,10,13,16,19-Docosahexaenoicacid (DHA, or Sigma D2534) and Elaidic acid (Caymen chemicals, cat #90250) were dissolved in standard medium (DMEM High Glucose, 10% FCS, 1% Pen-Strep) to a final concentration of 50 μM.

BEF cells were seeded in 6-Well plate, 50,000 cells/well and incubated at 38° C., 5% $CO_2$. Next day, after the cells adhered the plate surface, the medium containing Elaidic acid and DHA was added to cells. Cells incubated with the standard medium only served as a control. The medium was replaced every other day for 6 days. At the end of the assay, the cells were washed with PBS pH=7.4 and fixed with formaldehyde 4% buffer pH=7.4 for 20 min. The wells were washed three times with high volume of PBS pH=7.4. Oil Red 0 (Sigma 01391) working solution was added into each well for 15 min. The wells were washed three times with high volumes of $dH_2O$.

Figure 4:
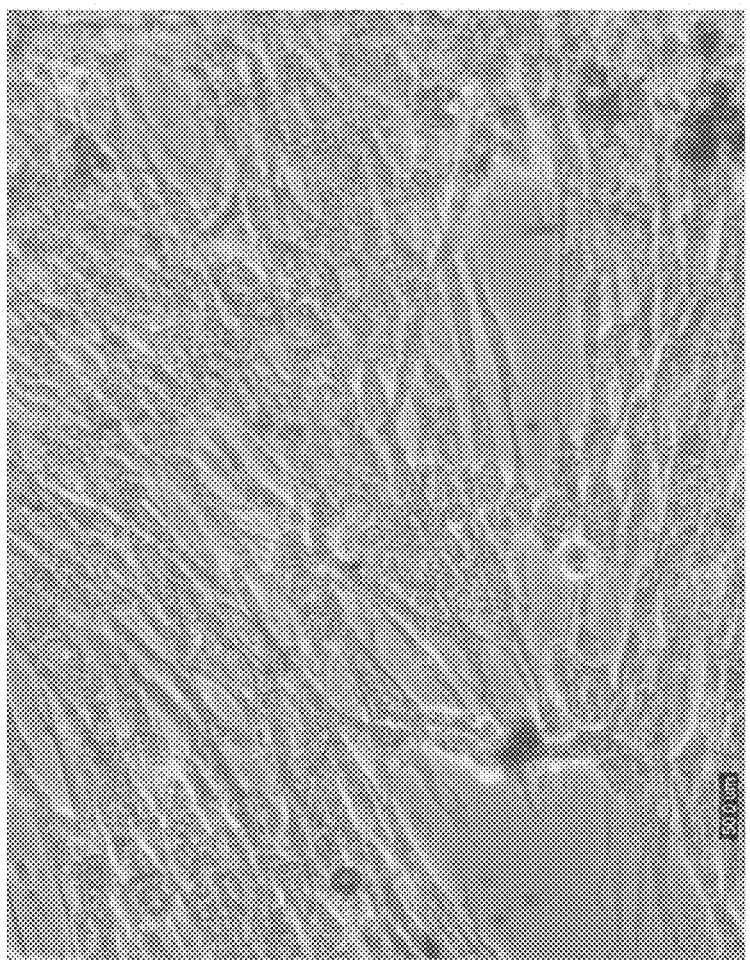
FIG. 4 shows a photograph of BEF cells exposed to a combination of Elaidic acid and DHA for 6 days. Lipid droplets (containing Oil Red O) appear as dark gray pots in the cells.

As can be seen in FIG. 4, cells treated with a medium containing Elaidic and DHA (in a ratio of 1:1) started to accumulate lipid droplets in the cells.

Oil Red O staining was semi-quantitatively measured. Oil Red O staining was extracted with 100% isopropanol for 5 min. The absorbance was measured at a wavelength of 492 nm. Significant staining was observed with a combination of Elaidic acid and DHA (OD 492 absorbance of 0.1207 compared to 0.0352 in the control).

Example 6: Lycopene Uptake

In one experiment, BEF cells at full confluence were incubated with Redivivo (Lycopene) 10% CWS/S-TG (DSM, Cat #5003792004) in standard medium (DMEM High Glucose, 10% FCS, 1% Pen-Strep) to a final concentration of 0.11 mg/ml, for 24 hours at 38° C., 5% $CO_2$.

The cells were then harvested by trypsinization and the pellet was washed three times with PBS. Cells pellet color was yellow. $13*10^6$ cells (weighting 147 mg) were analyzed in UPLC method. The quantitation of the carotenoid amounts in the cells was performed by comparing the sample to the reference—Redivivo (Lycopene) 10% CWS/S-TG.

Applying 0.11 mg/ml lycopene to the cells resulted in uptake of 10 μg Lycopene/gr cells, as can be seen in table 4 hereinbelow.

In additional experiment, BEM cells at full confluence were incubated with Resolute Ruby A Lycored (Cat #400280, another formula of soluble lycopene in water) in standard medium (DMEM High Glucose, 20% FCS, 1% Pen-Strep) to a final concentration of 0.002 mg/ml, for 24 hours at 38° C., 5% $CO_2$.

The cells were then harvested by trypsinization and the pellet was washed three times with PBS. Cells pellet color was dark red. $13*10^6$ cells (weighting 160 mg) were analyzed in UPLC method. The quantitation of the amounts of carotenoids in the cells was performed by comparing the sample to the reference—Resolute Ruby A Lycored.

As can be seen in table 4, applying 0.002 mg/ml lycopene to the cells resulted in uptake of 30 μg Lycopene/gr cells.

Dietary intake of lycopene varies greatly depending upon the studied population. The average Italian consumes 14.3 mg/day of total carotenoids (Lucarini et al. 2006). In the United States, the typical dietary intake of lycopene is about 2-5 milligrams (mg) per day (Krinsky and Johnson, 2005).

Example 7: Canthaxanthin Uptake

A mixture of BEF and BEM cells at full confluence were incubated with Canthaxanthin 10% CWS/S (Cat #5005256004) in standard medium (DMEM High Glucose, 10% FCS, 1% Pen-Strep) to a final concentration of 1.1 mg/ml for 24 hours at 38° C., 5% $CO_2$.

The cells were then harvested by trypsinization and the pellet was washed three times with PBS. Cells pellet color was red-orange. $20*10^7$ cells (weighting 855 mg) were analyzed in UPLC method. The quantitation of the carotenoid amounts in the cells was performed by comparing the sample to the reference—Canthaxanthin 10% CWS/S.

Applying 1.1 mg/ml Canthaxanthin to the cells resulted in uptake of 420 μg Canthaxanthin/gr cells, as can be seen in table 4.

According to Color Additives Approved for Use in Human Food part73, Subpart A: Color additives exempt from batch certification published by FDA, not to exceed 66 mg canthaxanthin per kg of solid or semisolid food or per pint of liquid food.

TABLE 4

Concentration of the carotene nutrients before and after BEF and BEM cells uptake

| Nutrient | Concentration of nutrient mixture in the medium (mg/ml) | Concentration of pure nutrient in the medium (mg/ml) | Concentration of pure nutrient in the cells (μg nutrient/gr cells) |
|---|---|---|---|
| Canthaxanthin | 10 | 1.1 | 420 |
| Lycored Ruby A | 10 | 0.002 | 30 |
| Redivivo | 1 | 0.11 | 10 |
| Beta carotene | 1 | 0.11 | 200 |

Example 8: Use of Yeast Extract for the Enrichment of Bovine Derived Cells Taste BEF cells at full confluence are incubated with yeast extract dissolved in standard medium (DMEM High Glucose, 10% FCS, 1% Pen-Strep) to final concentrations of 0.5% or 2%, respectively, for 24 hours at 38° C., 5% $CO_2$. Three types of yeast extract are examined: Yeast extract containing high glutamic acid yeast extract, e. g. Springer catalog No. 4101/0-PW-L and equivalent thereof; Yeast extract containing basic yeast extract, e. g. Springer catalog No. 04/02/20-MG and equivalent thereof, and Yeast extract containing high I+G yeast extract, e. g. Springer catalog No. 2012/20-MG-L AF and equivalent thereof.

The cells are then harvested by trypsinization and the pellet is washed three times with PBS. The cells pellet is analyzed by electronic nose and electronic tongue and compared to control (without yeast extract).

Artificial tongues often rely on measuring changes in electrical potential or current caused by the target molecule reacting with a receptor. These devices are therefore often called electronic tongues, or e-tongues, and work in a similar way to a natural tongue. Artificial tongues can sense: bitterness, sourness, saltiness, umami(savory) and sweetness. Exemplary taste sensors are commercialized taste sensing systems SA 402B and TS-5000Z (Kiyoshi Toko. 2012. Nature 486:S18-S19 doi:10.1038/486518a).

Electronic noses were engineered to mimic the mammalian olfactory system within an instrument designed to obtain repeatable measurements, allowing identifications and classifications of aroma mixtures. An electronic nose system typically consists of a multisensor array, an information-processing unit—an artificial neural network (ANN), software with digital pattern-recognition algorithms, and reference-library databases. Hundreds of different prototypes of artificial-nose devices have been developed (See, e.g. Wilson A D and Baietto M. 2009. Sensors 9:5099-5148; doi:10.3390/s90705099).

Example 9: Uptake of a Combination of Vitamin B12, Canthaxanthin, and Lycopene

In one experiment, a mixture of vitamin B12 (Sigma, Cat #V2876); Canthaxanthin 10% CWS/S (Cat #5005256004); and Lycopene Resolute Ruby A (Lycored, Cat #400280) in pure water, at final concentrations as presented in Table 5 below, was prepared. The color of the supplement mixture was measured for L* a* b* parameters by colorimeter, according to the guidelines published by the American Meat Science Association. The parameters were compared to values of for L* a* b* from meat cut, and were found to be comparable (Table 6).

TABLE 5

Colorants mixture concentrations

| Sample No./ Concentration (mg/ml) | Redivivo | Canthaxanthin | Vitamin B12 | Resolute Ruby A |
|---|---|---|---|---|
| 1 | 0.9 | 3.5 | 0.5 | — |
| 2 | 0.35 | 1.75 | 4.6 | — |
| 3 | — | 1.75 | 0.5 | 1 |

TABLE 6

Color comparison of a supplement mixture and fresh meat cuts

| Sample | L* | a* | b* | C* | h |
|---|---|---|---|---|---|
| Sinta cut | 33.87 | 21.61 | 11.35 | 24.41 | 27.67 |
| Beef shoulder | 36.23 | 24.30 | 14.19 | 28.15 | 30.25 |
| Beef steak | 41.43 | 21.26 | 14.92 | 25.99 | 35.11 |

TABLE 6-continued

Color comparison of a supplement mixture and fresh meat cuts

| Sample | L* | a* | b* | C* | h |
|---|---|---|---|---|---|
| (Entrecôte) | | | | | |
| Sample 1 | 30.70 | 29.57 | 21.73 | 36.69 | 36.32 |
| Sample 2 | 23.60 | 22.22 | 11.34 | 24.94 | 27.03 |
| Sample 3 | 27.79 | 24.49 | 17.99 | 30.38 | 36.30 |

Fully confluent BEF cells are incubated with the above-described supplement mixture for 24 hours at 38° C., 5% $CO_2$.

The cells were then harvested by trypsinization and the pellet is washed three times with PBS. Cells pellet color is analyzed by setting L*a*b* or L*C*h parameters by colorimeter.

In another experiment, a supplement mixture containing vitamin B12 (Sigma, Cat #V2876); Canthaxanthin 10% CWS/S (Cat #5005256004); Redivivo Lycopen 10% CWS/S-TG (Cat #5003792004) in pure water to final concentrations of 0.5 mg/ml, 3.5 mg/ml, 0.9 mg/ml respectively is prepared. The mix of nutrients (Vitamin B12, Canthaxanthin and Lycopene) color is measured for L* a* b* parameters by colorimeter. The parameters are compared to values of for L* a* b* from lean meat cut.

Fully confluent BEF cells are incubated with the above-described supplement mixture for 24 hours at 38° C., 5% $CO_2$. The cells are then harvested by trypsinization and the pellet is washed three times with PBS. Cells pellet color is analyzed by UPLC method and/or by setting the L* a* b* or L*C*h parameters by colorimeter.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A non-human-animal derived cell culture comprising a plurality of non-human animal-derived cells, wherein at least 60% of the cells comprise a combination of exogenous supplements consisting of cobalamin (B12) and at least one natural colorant selected from the group consisting of alpha-carotene, beta-carotene, lycopene, canthaxanthin, and anthocyanin, and, optionally, at least one additional exogenous supplement selected from the group consisting of iron and/or a salt thereof, yeast extract, bacterial extract, folate (vitamin B9), zinc and/or a salt thereof, selenium and/or a salt thereof, vitamin D, vitamin E, Coenzyme Q10, at least one fatty acid, and a flavoring agent, wherein the combination of exogenous supplements is present in the intracellular space, intramembrane space, on the cell membrane, or any combination thereof upon uptake and accumulation and/or adherence of the exogenous supplement in or on the cells, in an amount sufficient to confer a meat-like color to the non-human-animal derived cell culture, wherein said meat-like color is characterized by the three primary color receptors of the human eye quantified into coordinate values of L*a*b* by colorimeter, wherein the L* value is from about 23 to about 42, the a* value is from about 21 to about 30, and the b* value is from about 11 to about 22.

2. The non-human-animal derived cell culture of claim 1, wherein the non-human animal-derived cells comprise at least one compound having absorbance at a wavelength or a plurality of wavelengths of from about 300 nm to about 700 nm.

3. The non-human-animal derived cell culture of claim 1, wherein the non-human animal-derived cells comprise a combination of the at least one natural colorant, vitamin B12 and iron and/or a salt thereof.

4. The non-human-animal derived cell culture of claim 1, wherein the non-human animal derived cells are pluripotent stem cells (PSCs) and/or cells differentiated therefrom.

5. The non-human-animal derived cell culture of claim 1, wherein the non-human animal derived cells are induced pluripotent stem cells (iPSCs) reprogrammed from somatic non-human animal cells and/or cells differentiated therefrom.

6. The non-human-animal derived cell culture of claim 1, wherein the non-human animal derived cells are non-embryonic stem cells (ESCs).

7. The non-human-animal derived cell culture of claim 1, wherein the non-human animal derived cells are satellite cells.

8. The non-human-animal derived cell culture of claim 1, wherein the non-human-animal derived cells are selected from the group consisting of muscle cells and progenitors thereof; fat cells and progenitors thereof; stromal cells and progenitors thereof; endothelial cells and progenitors thereof; and any combination thereof.

9. Cultured meat comprising the non-human-animal derived cell culture of claim 1.

10. The cultured meat of claim 9, said cultured meat further comprises an edible scaffold.

* * * * *